(12) United States Patent
Sato et al.

(10) Patent No.: US 10,608,365 B2
(45) Date of Patent: Mar. 31, 2020

(54) TERMINAL PROTECTION PARTS

(71) Applicant: SHARP KABUSHIKI KAISHA, Sakai, Osaka (JP)

(72) Inventors: Tadahiko Sato, Sakai (JP); Yan Qian, Sakai (JP); Hitoshi Aoki, Sakai (JP)

(73) Assignee: SHARP KABUSHIKI KAISHA, Sakai, Osaka (JP)

( * ) Notice: Subject to any disclaimer, the term of this patent is extended or adjusted under 35 U.S.C. 154(b) by 0 days.

(21) Appl. No.: 16/293,367

(22) Filed: Mar. 5, 2019

(65) Prior Publication Data
US 2019/0305465 A1  Oct. 3, 2019

(30) Foreign Application Priority Data
Mar. 30, 2018  (JP) ................. 2018-069143

(51) Int. Cl.
*H01R 13/447* (2006.01)
*G02B 23/24* (2006.01)
*A61B 1/04* (2006.01)
*A61B 1/00* (2006.01)
*H01R 13/44* (2006.01)

(52) U.S. Cl.
CPC ....... *H01R 13/447* (2013.01); *A61B 1/00002* (2013.01); *A61B 1/04* (2013.01); *G02B 23/24* (2013.01); *H01R 13/44* (2013.01)

(58) Field of Classification Search
CPC .............................. H01R 13/44; H01R 13/447
See application file for complete search history.

(56) References Cited

U.S. PATENT DOCUMENTS

| | | | | |
|---|---|---|---|---|
| 6,908,342 B2* | 6/2005 | Shimada | ........... | H01R 13/453 |
| | | | | 439/136 |
| 6,932,629 B2* | 8/2005 | Ikenoue | ........... | H01R 13/447 |
| | | | | 439/136 |
| 7,341,464 B2* | 3/2008 | Cuellar | ........... | H01R 13/447 |
| | | | | 439/135 |
| 8,085,544 B2* | 12/2011 | Zhao | ........... | H01R 13/447 |
| | | | | 235/441 |
| 9,431,778 B1* | 8/2016 | Mueller | ........... | H01R 13/447 |
| 10,128,604 B2* | 11/2018 | Li | ........... | H01R 13/447 |
| 2010/0311258 A1* | 12/2010 | Su | ........... | H01R 13/5213 |
| | | | | 439/136 |

FOREIGN PATENT DOCUMENTS

JP    H10-225439 A    8/1998

* cited by examiner

*Primary Examiner* — Tho D Ta
(74) *Attorney, Agent, or Firm* — ScienBiziP, P.C.

(57) ABSTRACT

A connector unit includes a connector cap and a camera-side cable connector. The connector cap includes a connection portion that movably connects the connector cap to the camera-side cable connector. The camera-side cable connector includes a first groove in which a protruding section of the connection portion is movably disposed.

9 Claims, 19 Drawing Sheets

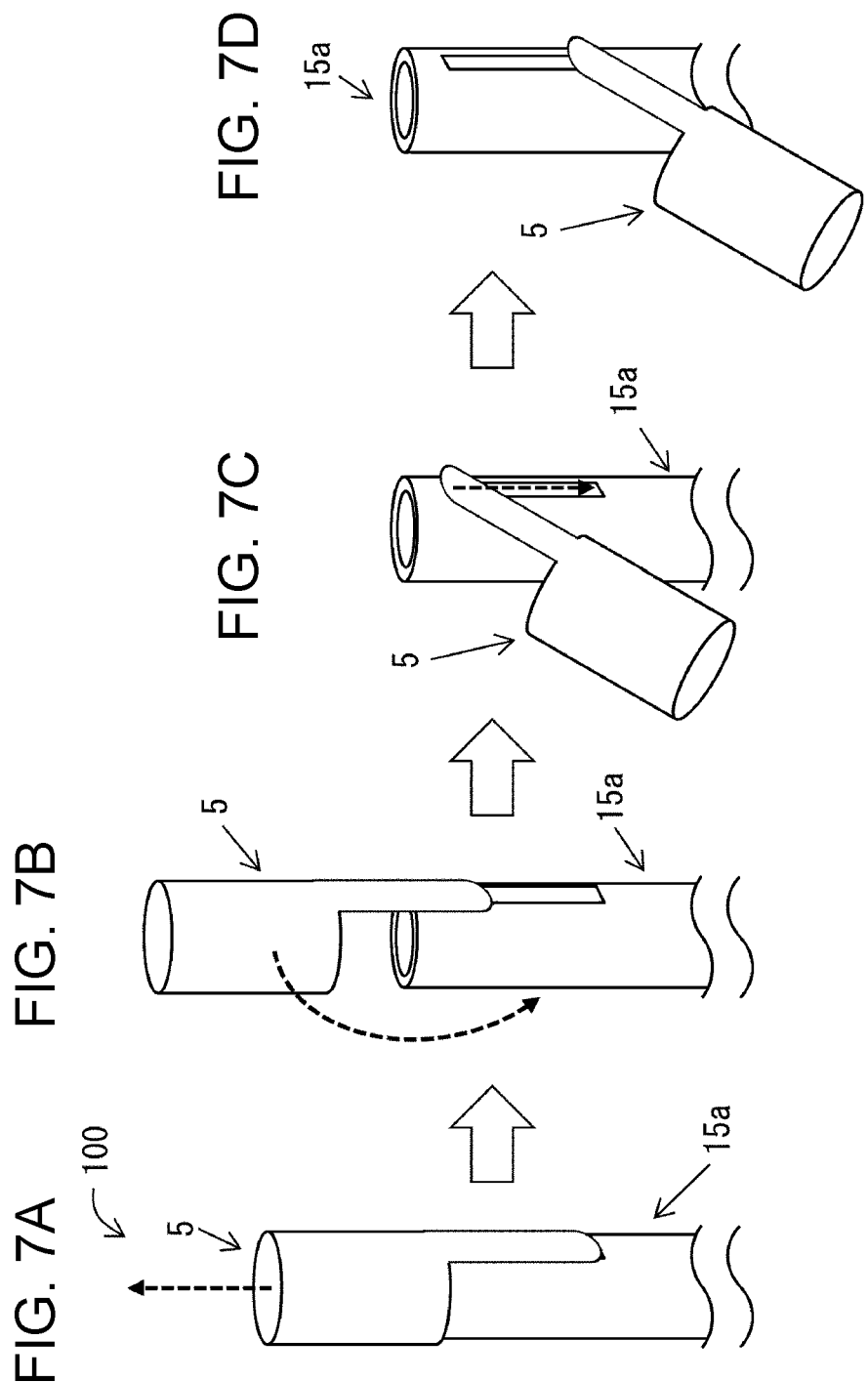

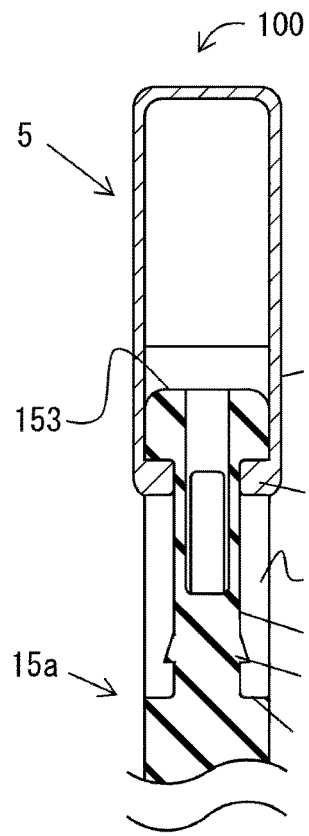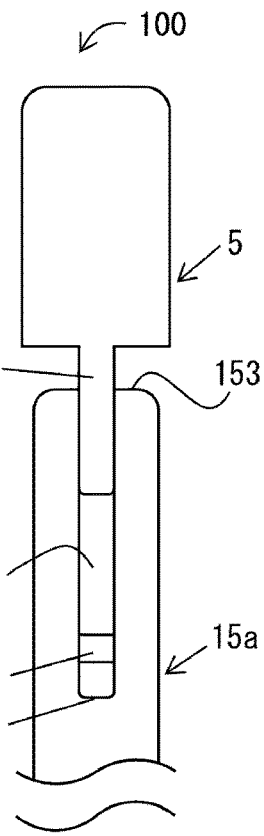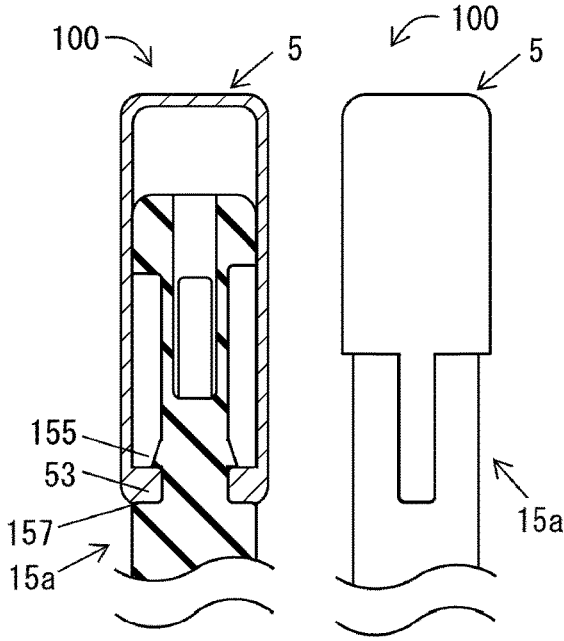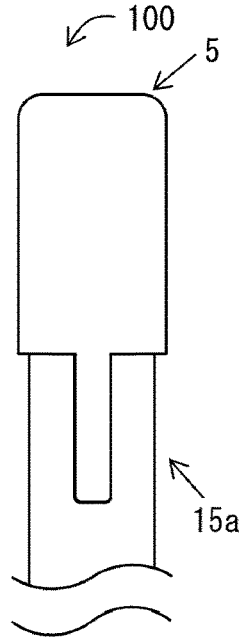
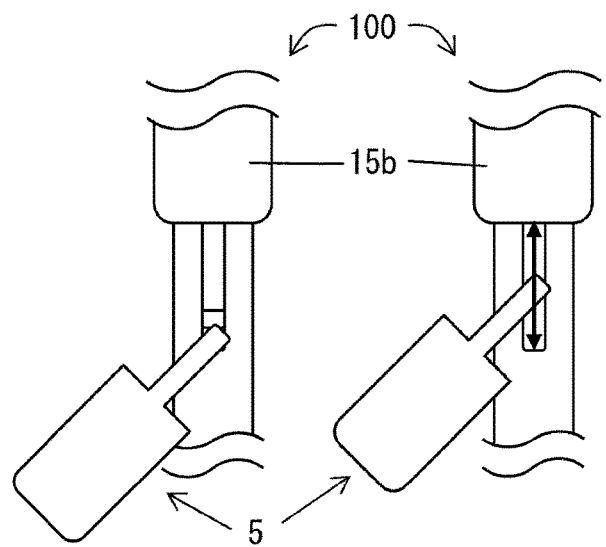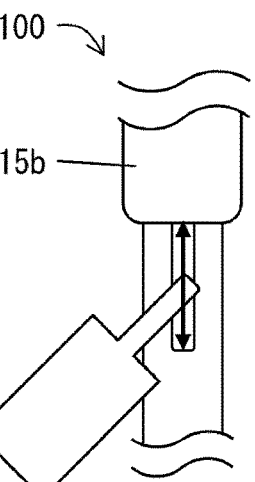

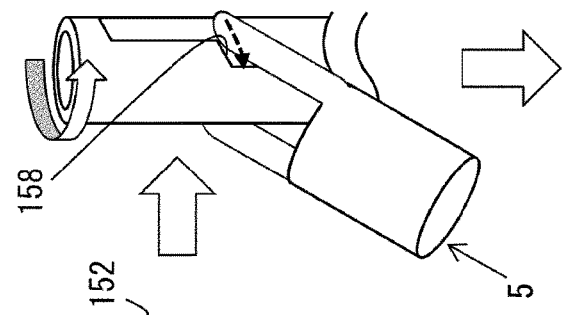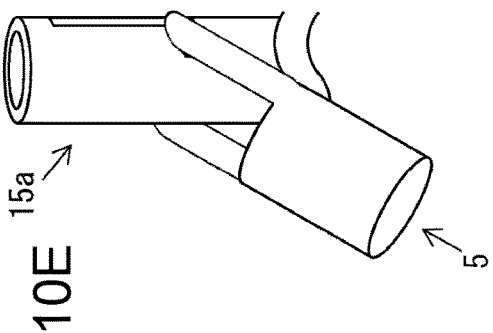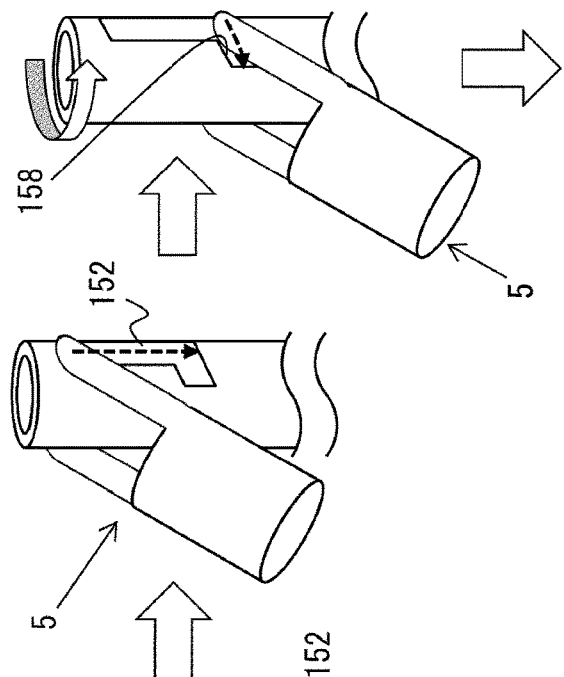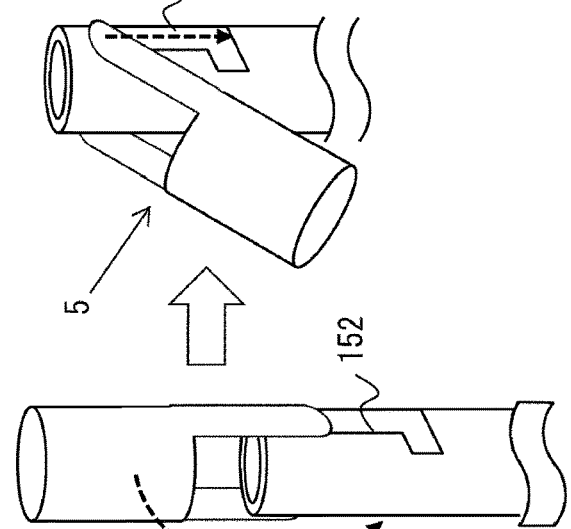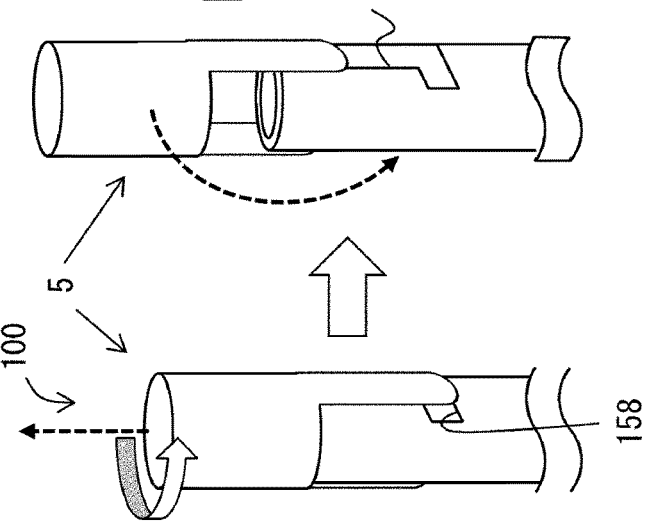

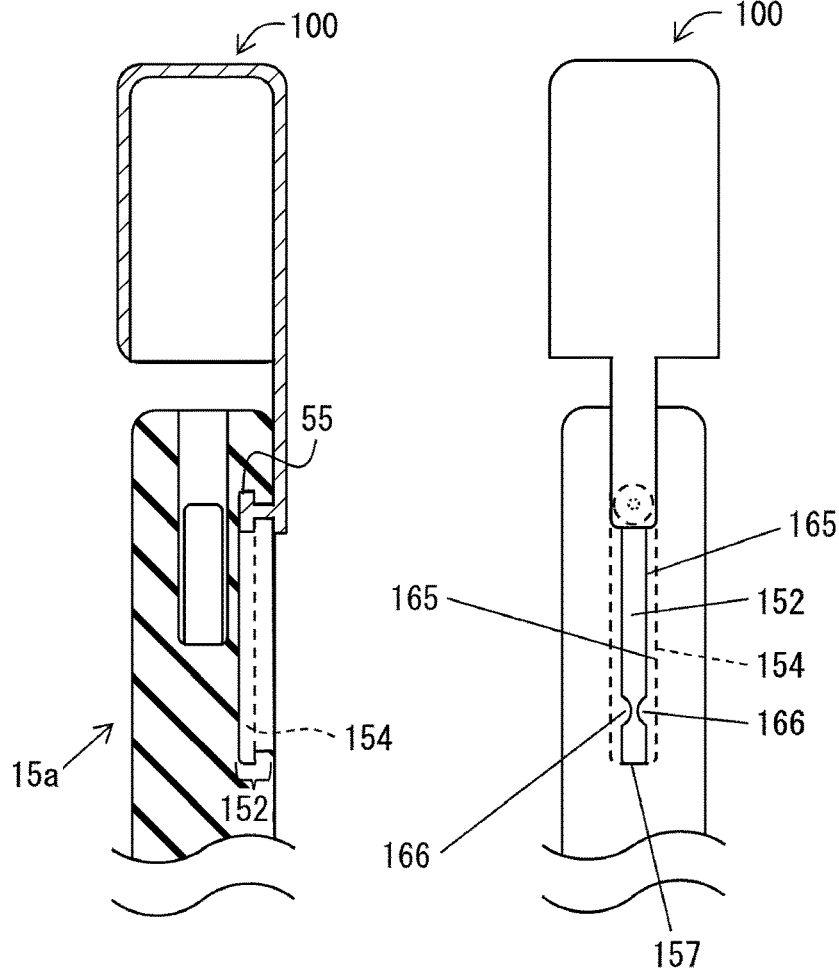
FIG. 12D 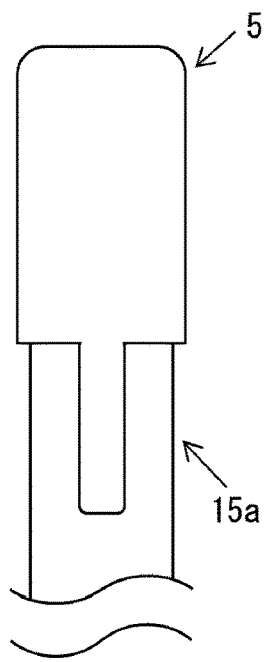   FIG. 12E 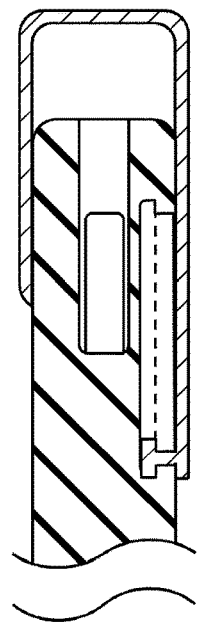

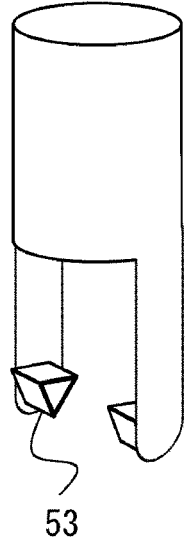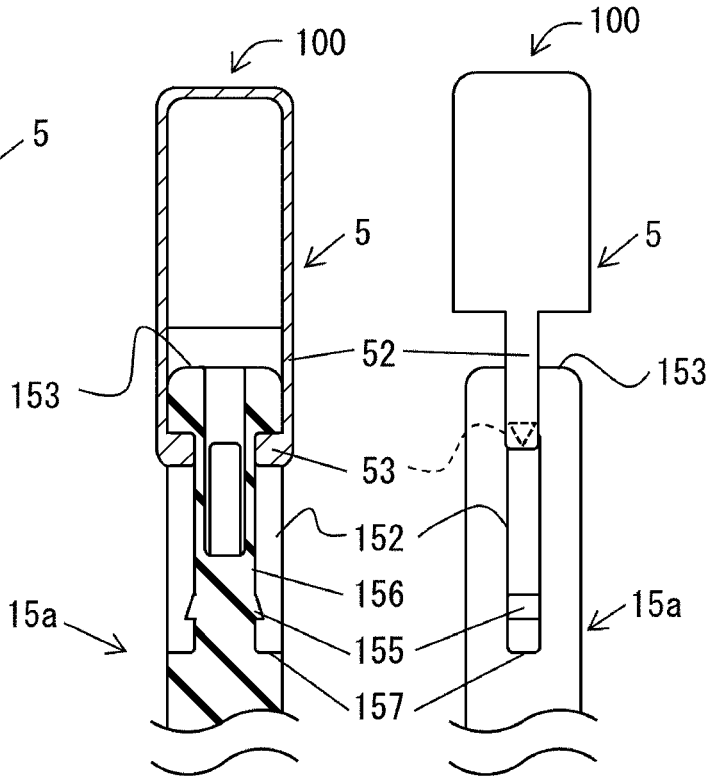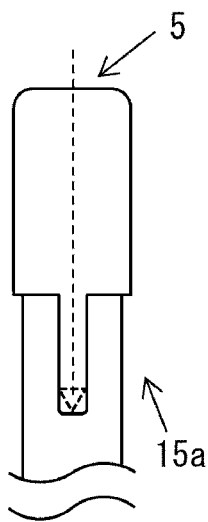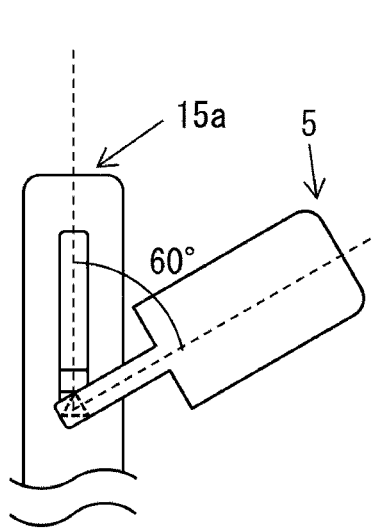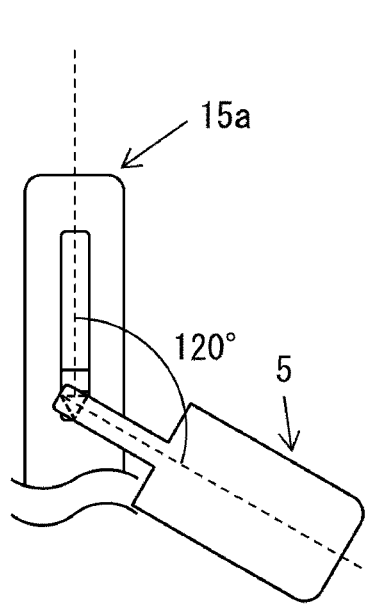
FIG. 13A  FIG. 13B  FIG. 13C
FIG. 13D  FIG. 13E  FIG. 13F FIG. 14A
FIG. 14B
FIG. 14C
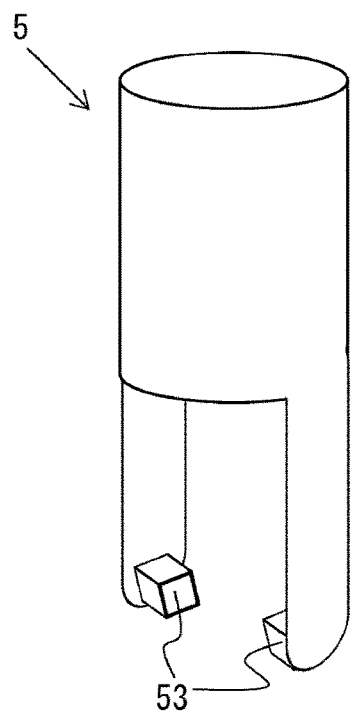
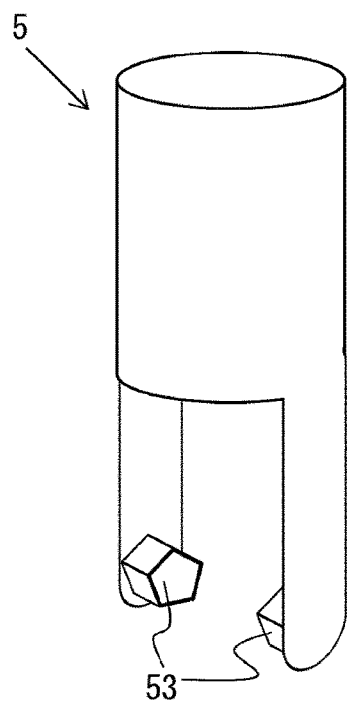
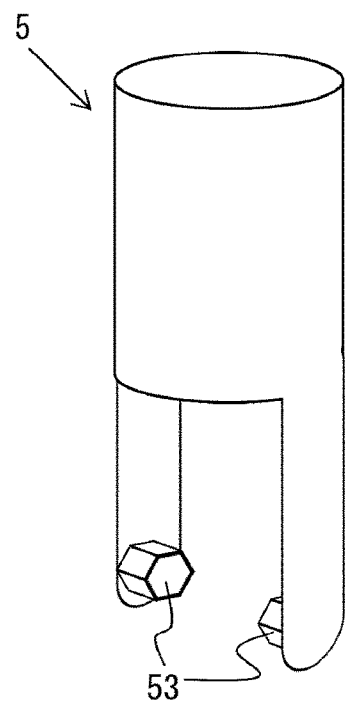

FIG. 15A
FIG. 15B
FIG. 15C
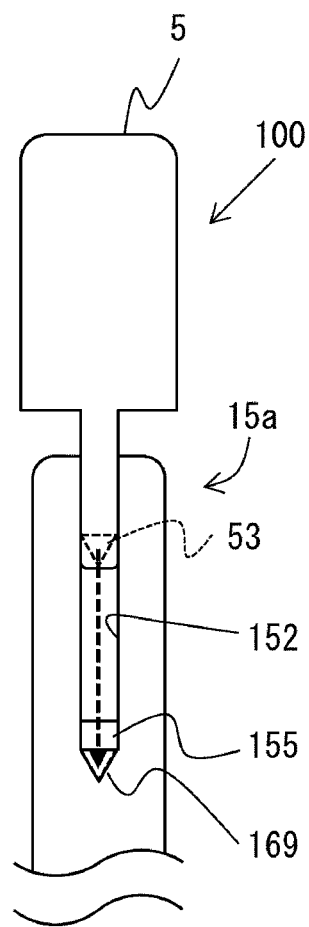
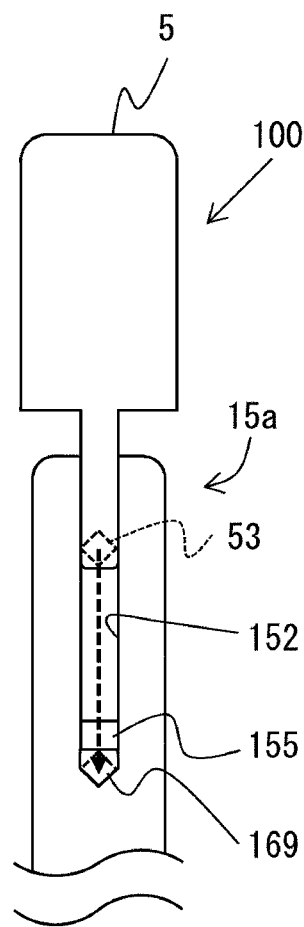
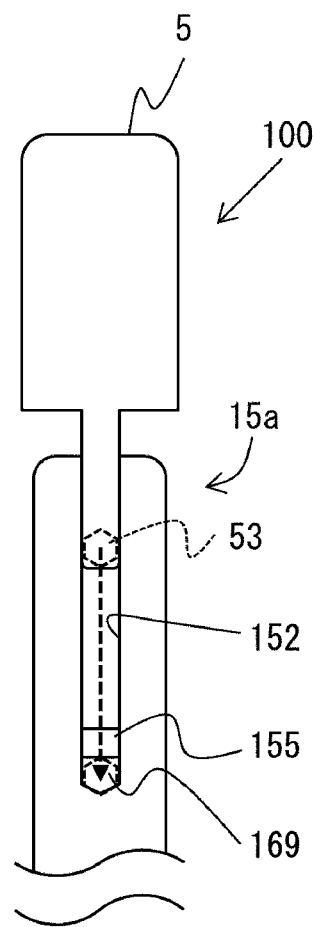
FIG. 15D
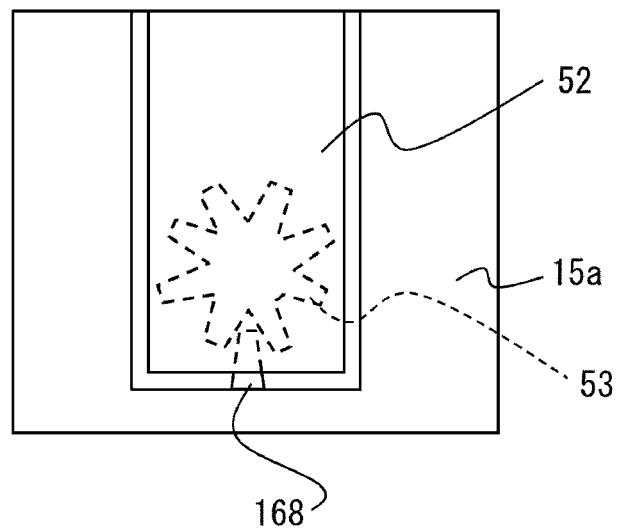

TERMINAL PROTECTION PARTS

BACKGROUND

1. Field

The present disclosure relates to a connector unit including a connector and a connector cap that is removably attached to the connector.

2. Description of the Related Art

For example, when a connector, for electrically connecting an electronic device to a controller of the electronic device, is in an unconnected state, it may be necessary to attach a connector cap to the connector.

Japanese Unexamined Patent Application Publication No. 10-225439 (laid open on Aug. 25, 1998) describes a structure of an endoscopic imaging device for appropriately holding a waterproof cap so that the cap may not interfere with an operation environment.

Depending on the use of an electronic device, it may be necessary to attach a connector cap to a connector in a process of setting the electronic device or in a process of removing the electronic device. However, Japanese Unexamined Patent Application Publication No. 10-225439 does not describe a structure that enables a connector cap to be attached to a connector in the process of setting the electronic device or in the process of removing the electronic device.

It is desirable to provide a connector unit that enables a connector cap to be easily attached to and removed from a connector while preventing the connector cap from becoming lost and from being forgotten to be attached to the connector.

SUMMARY

According to an aspect of the disclosure, there is provided a connector unit including a connector, and a tubular connector cap that is removably attached to the connector and whose distal end is closed. The connector cap includes a connection portion at an end thereof adjacent to an opening thereof, and the connection portion movably connects the connector cap to the connector. The connection portion is movably connected to the connector in a state in which a concave portion included in one of a side wall of the connector and the connection portion and a convex portion included in the other of the side wall and the connection portion are fitted to each other. In a state in which the connector cap is attached to the connector, a distal end portion of the connector is inserted from the opening into a space in the connector cap.

BRIEF DESCRIPTION OF THE DRAWINGS

FIGS. 7A to 7D are schematic views illustrating an example of an operation of removing a connector cap from a distal end portion of a connector according to the second embodiment of the present disclosure;

FIGS. 8A to 8E illustrate an example of a connector unit according to a third embodiment of the present disclosure, and FIG. 8F illustrates a reference example of a connector unit compared with the third embodiment;

FIGS. 10A to 10E are schematic views illustrating an example of an operation of removing a connector cap from a distal end portion of a connector according to the fourth embodiment of the present disclosure;

FIGS. 12A to 12E illustrate an example of a connector unit according to a fifth embodiment of the present disclosure;

FIGS. 13A to 13F illustrate an example of a connector unit according to a sixth embodiment of the present disclosure;

FIGS. 14A to 14C illustrate examples of protruding sections according to the sixth embodiment having other shapes;

FIGS. 15A to 15C illustrate examples of a connector unit according to a modification of the sixth embodiment of the present disclosure, and FIG. 15D illustrates an example of a protruding section according to another modification of the sixth embodiment of the present disclosure;

DESCRIPTION OF THE EMBODIMENTS

First Embodiment

Hereinafter, a first embodiment of the present disclosure will be described in detail.

Connector Unit 100

Figure 3:
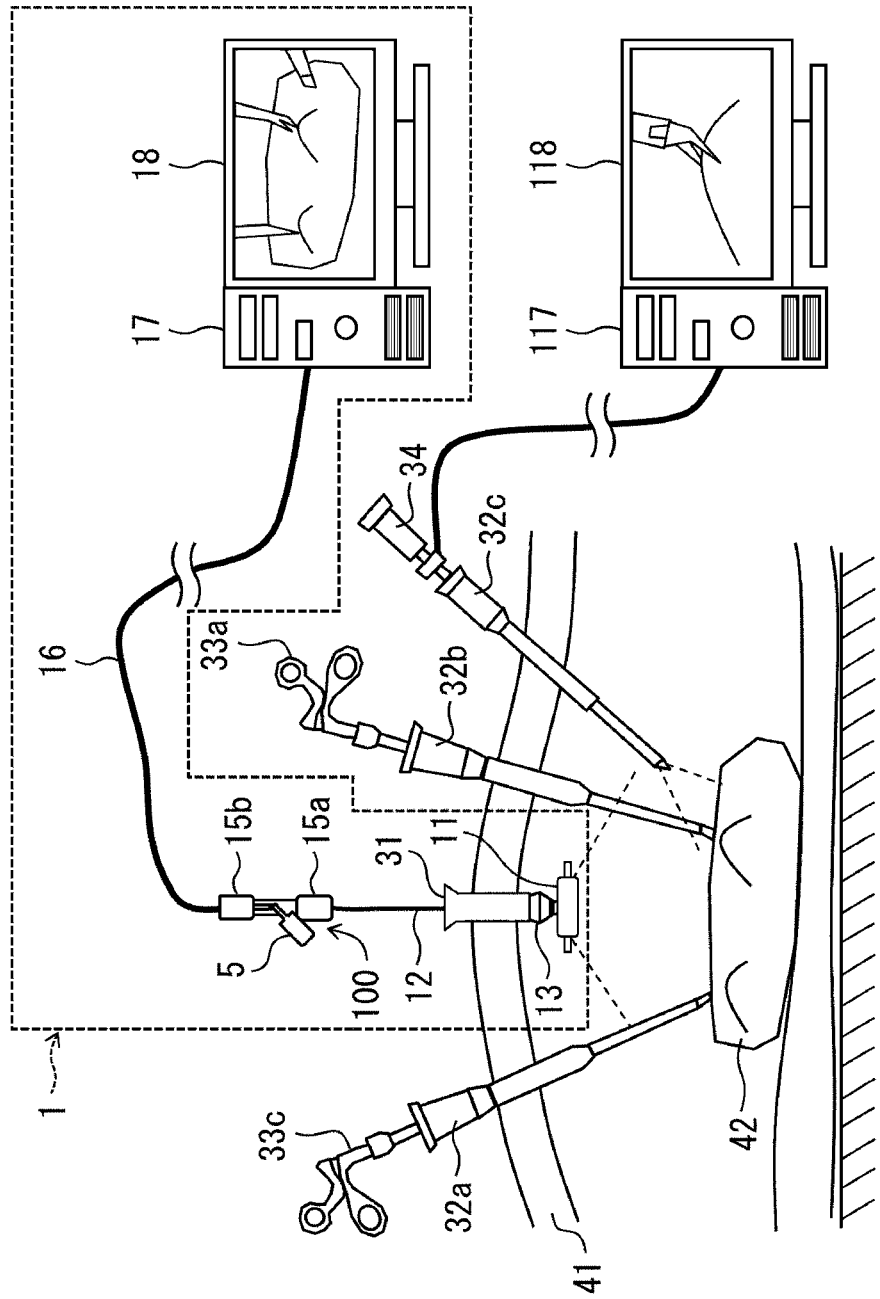
FIG. 3 is a schematic view of an example of an intracorporeal monitoring camera system according to the first embodiment of the present disclosure.

FIG. 3 is a schematic view of an example of an intracorporeal monitoring camera system 1 according to the present embodiment. In the present embodiment, an example in which a connector unit 100 is used for the intracorporeal monitoring camera system 1 will be described. As illustrated in FIG. 3, a camera unit 11 is set inside an abdominal wall 41, that is, in a body. When setting the camera unit 11 in the body, a camera-side cable connector 15a is temporarily inserted into the body and then pulled out of the body. When removing the camera unit 11 out of the body, the camera-side cable connector 15a is temporarily inserted into the body and then pulled out of the body. In the process of setting the camera unit 11 or in the process of removing the camera unit 11, if a terminal of the camera-side cable connector 15a becomes wet in the body, contact failure of the camera-side cable connector 15a may occur. Therefore, before inserting the camera-side cable connector 15a into the body, a connector cap 5 is attached to the camera-side cable connector 15a.

Figure 1A:
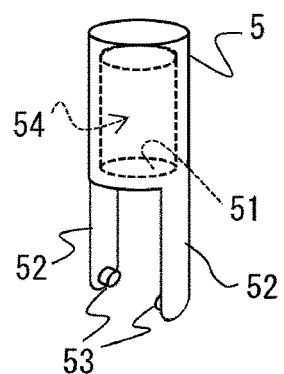
FIGS. 1A to 1E are perspective views of an example of a connector unit according to a first embodiment of the present disclosure.
Figure 1B:
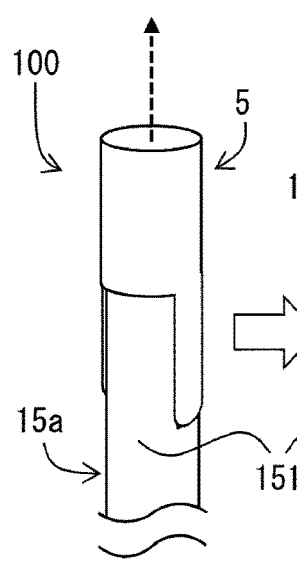

FIGS. 1A to 1E are perspective views of an example of the connector unit 100 according to the present embodiment. As illustrated in FIG. 1B, the connector unit 100 includes the camera-side cable connector 15a and the connector cap 5, which is attachable to and removable from the camera-side cable connector 15a. The connector cap 5 has a tubular shape whose distal end is closed.

Camera-Side Cable Connector 15a

The camera-side cable connector 15a is fitted into a device-side cable connector 15b to connect a camera-side cable 12 to a device-side cable 16. The camera-side cable connector 15a includes terminals that are used for the connection.

As illustrated in FIGS. 1B to 1E, a side wall 151 of the camera-side cable connector 15a has first grooves 152 (concave portion). The first grooves 152 extend in the axial direction of the camera-side cable connector 15a and open outward. In the present embodiment, the camera-side cable connector 15a has two first grooves 152 that face each other with the central axis of the camera-side cable connector 15a therebetween.

Connector Cap 5

The connector cap 5 is attached to the camera-side cable connector 15a to protect the terminals and other components of the camera-side cable connector 15a. As illustrated in FIG. 1A, the connector cap 5 includes connection portions 52 at an end adjacent to an opening 51. The connection portions 52 movably connect the connector cap 5 to the camera-side cable connector 15a. To be specific, as illustrated in FIG. 1A, the connection portions 52 extend in the axial direction of the connector cap 5 from the end adjacent to the opening 51. In the present embodiment, the connector cap 5 has two connection portions 52 that face each other with the central axis of the connector cap 5 therebetween. The connection portions 52 each have a protruding section 53 (convex portion) that protrudes toward the central axis of the camera-side cable connector 15a. The protruding sections 53 are movably disposed in the first grooves 152 of the camera-side cable connector 15a.

As illustrated in FIG. 1B, in a state in which the connector cap 5 is attached to the camera-side cable connector 15a, a distal end portion 153 of the connector is inserted from the opening 51 of the connector cap 5 into a space 54 in the connector cap 5.

With the structure described above, because the protruding sections 53 are movably disposed in the first grooves 152, the protruding sections 53 can be moved in the axial direction of the connector in the first grooves 152. Moreover, the protruding sections 53 can be rotated in the first grooves 152.

Operation of Removing Connector Cap 5 from Distal End Portion of Camera-Side Cable Connector 15a

Referring to FIGS. 1B to 1E, an example of an operation of removing the connector cap 5 from a distal end portion of the camera-side cable connector 15a will be described.

Figure 1C:
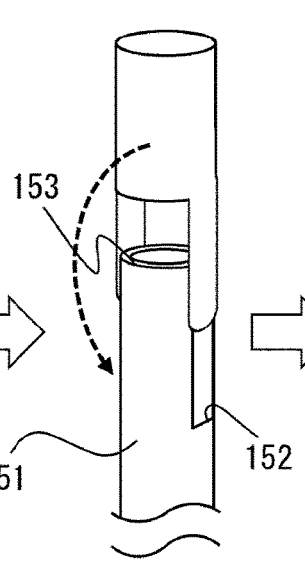
Figure 1D:
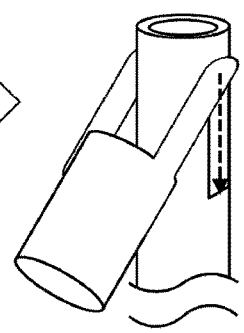
Figure 1E:
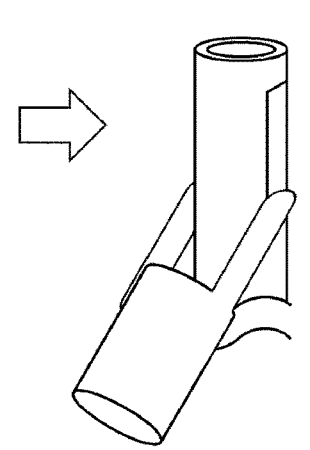

A user moves (slides) the connector cap 5 in a direction away from the camera-side cable connector 15a so that the state of the connector cap 5 changes from a state shown in FIG. 1B to a state shown in FIG. 1C. Due to the user's operation, the connector cap 5 is removed from the distal end portion 153 of the camera-side cable connector 15a. Next, the user rotates the connector cap 5 relative to the camera-side cable connector 15a so that the state of the connector cap 5 changes from a state shown in FIG. 1D to a state shown in FIG. 1E. Due to the user's operation, the protruding sections 53 rotate in the first grooves 152. Moreover, the user slides the position of the connector cap 5 toward a proximal end of the camera-side cable connector 15a so that the state of the connector cap 5 changes from a state shown in FIG. 1D to a state shown in FIG. 1E. Due to the user's operation, the position of the connector cap 5 can be moved to a predetermined position relative to the camera-side cable connector 15a. A user can attach the connector cap 5 to the distal end portion of the camera-side cable connector 15a by performing the aforementioned operation in reverse order.

That is, a user can attach the connector cap 5 to and remove the connector cap 5 from the camera-side cable connector 15a by performing the following operations: an operation of displacing the connector cap 5 relative to the camera-side cable connector 15a in the axial direction of the camera-side cable connector 15a; and an operation of rotating the connector cap 5 relative to the camera-side cable connector 15a. Therefore, a user can easily attach the connector cap 5 to and remove the connector cap 5 from the camera-side cable connector 15a.

In the structure described above, the camera-side cable connector 15a and the connector cap 5 are integrated. Thus, it is possible to prevent the connector cap 5 from becoming lost and from being forgotten to be attached to the camera-side cable connector 15a.

With the structure described above, when the connector cap 5 is attached to the camera-side cable connector 15a, the distal end portion 153 of the camera-side cable connector 15a is covered by the connector cap 5. Accordingly, for example, compared with a connector cap that is structured to cover only an opening at the distal end of the camera-side cable connector 15a, the connector cap 5 can be stably attached and can shield a larger area at the distal end of the connector from the outside. Therefore, it is possible to effectively prevent, for example, the following: unintended removal of the connector cap 5 from the camera-side cable connector 15a; and image blur or the like that may occur due to contact failure, short circuit, or the like when a bodily fluid, a body tissue, or the like adheres to a terminal at the distal end of the camera-side cable connector 15a.

In the present specification, the term "removal" refers to separation of a connector cap from a distal end portion of the connector while maintaining a state in which the connector cap is removably attached to the distal end portion of the connector.

As will be described below in detail in "Method of setting Camera Unit 11 in Body", the connector unit 100 may be inserted into or pulled out of the body through a small-diameter trocar. Therefore, the outside diameter of the connector cap 5 may be substantially the same as the outside diameter of the camera-side cable connector 15a.

Other Examples

FIGS. 2A to 2G are perspective views of another example of the connector unit 100 according to the present embodiment.

Figure 2A:
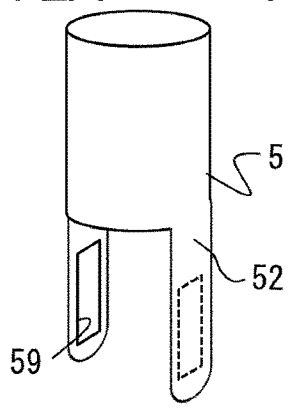
FIGS. 2A to 2E are perspective views of another example of a connector unit according to the first embodiment of the present disclosure.
Figure 2B:
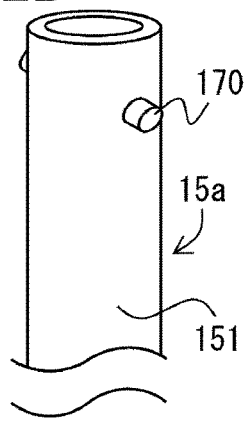

In the example shown in FIG. 1, the camera-side cable connector 15a includes the first grooves 152, and the connector cap 5 includes the protruding sections 53. In the present example, as illustrated in FIGS. 2A and 2B, the camera-side cable connector 15a includes protruding sections 170, which protrude outward, on the side wall 151. The connector cap 5 includes first grooves 59 in which the protruding sections 53 are movably disposed.

Figure 2C:
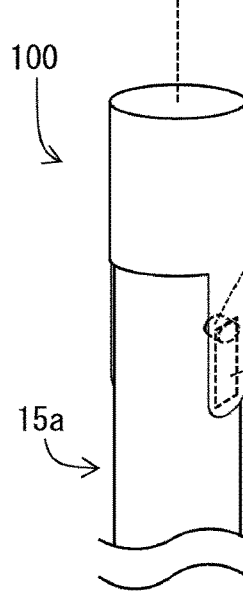
Figure 2D:
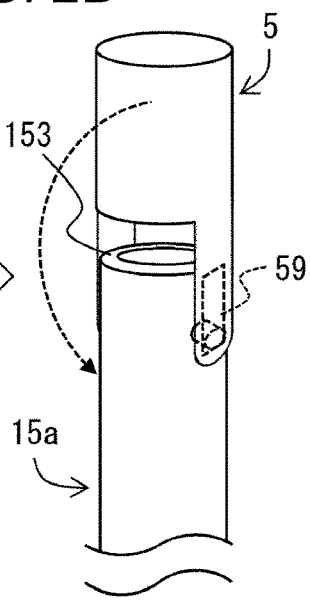
Figure 2E:
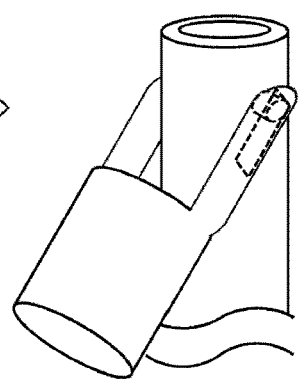

FIGS. 2C to 2E illustrate an example of an operation of removing the connector cap 5 from the distal end portion of the camera-side cable connector 15a. A user moves (slides) the connector cap 5 in a direction away from the camera-side cable connector 15a so that the state of the connector cap 5 changes from a state shown in FIG. 2B to a state shown in FIG. 2C. Due to the user's operation, the connector cap 5 is removed from the distal end portion 153 of the camera-side cable connector 15a. Next, the user rotates the connector cap 5 relative to the camera-side cable connector 15a so that the state of the connector cap 5 changes from a state shown in FIG. 2D to a state shown in FIG. 2E. Due to the user's operation, the protruding sections 170 rotate in the first grooves 59. Due to the user's operation, the position of the connector cap 5 can be moved to a predetermined position relative to the camera-side cable connector 15a.

Figure 2F:
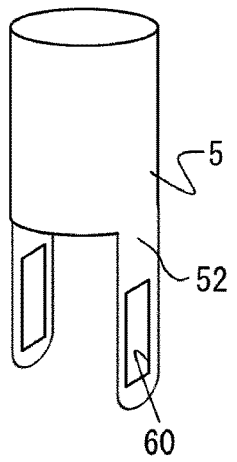
FIGS. 2F and 2G are perspective views of still another example of the connector unit.
Figure 2G:
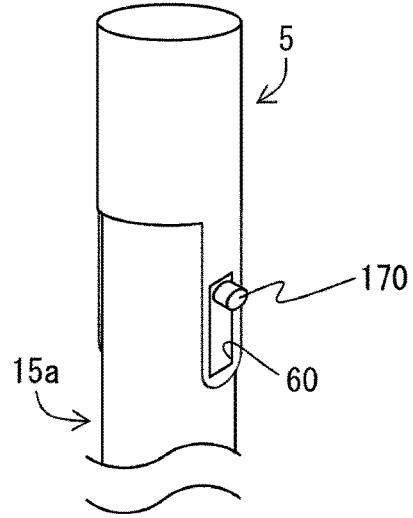

As illustrated in FIGS. 2F and 2G, the connector cap 5 may include slits 60, instead of the first grooves 59.

Also in embodiments described below, the camera-side cable connector 15a may include protruding sections, and the connector cap 5 may include first grooves or the like in which the protruding sections are movably disposed. That is, the connection portion 52 is movably connected to the camera-side cable connector 15a in a state in which a concave portion of one of the side wall 151 of the camera-side cable connector 15a and the connection portion 52 and a convex portion of the other of the side wall 151 and the camera-side cable connector 15a are fitted to each other.

Intracorporeal Monitoring Camera System 1

Referring to FIG. 3, details of the intracorporeal monitoring camera system 1 will be described. The intracorporeal monitoring camera system 1 is a medical system. As illustrated in FIG. 3, the intracorporeal monitoring camera system 1 includes the camera unit 11 (intracorporeal imaging device), which includes the camera-side cable 12 and which is to be placed in a body; a camera support pipe 13 that is used for connection with a trocar 31 (pipe-shaped device) inserted into the body; a control system that includes a camera unit controller 17 and a display 18 (display device); and the device-side cable 16, which connects the camera-side cable 12 and the camera unit controller 17 to each other.

The camera-side cable 12 has the camera-side cable connector 15a at an end opposite to a connection end that is connected to the camera unit 11. The device-side cable 16 has the device-side cable connector 15b at an end opposite to a connection end that is connected to the camera unit controller 17.

In the intracorporeal monitoring camera system 1, an intracorporeal end of the trocar 31 inserted through the abdominal wall 41 and the camera support pipe 13 are connected to each other. The camera unit 11 placed in the body and the support pipe are joined to each other, and the camera-side cable connector 15a is pulled out of the body through the camera support pipe 13 and the trocar 31.

Figure 4A:
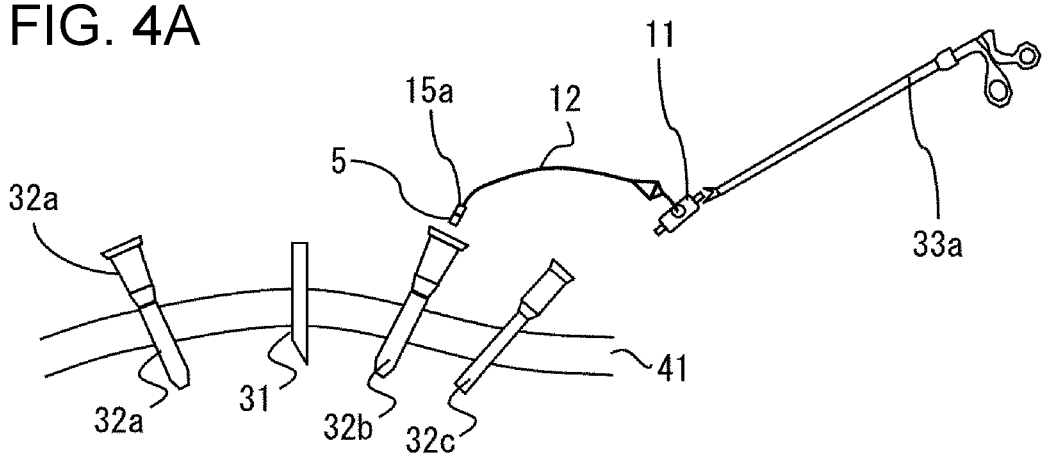
FIGS. 4A to 4F are schematic views illustrating an example of a method of setting a camera unit according to the first embodiment of the present disclosure in a body.

Method of Setting Camera Unit 11 in Body and Method of Removing Camera Unit 11 Out of Body Next, details of a method of setting the camera unit 11 in a body will be described. FIGS. 4A to 4F are schematic views illustrating an example of the method of setting the camera unit 11 in the body. As illustrated in FIG. 4A, first, an operator forms hole (ports), for inserting forceps and an endoscope into a body cavity, in the abdominal wall 41, and inserts trocars 32a to 32c into the ports. Moreover, in order to set the camera unit 11 in the body cavity, the operator forms a port in the abdominal wall 41 at a position from which the entirety of an organ having an affected area can be viewed, and inserts the trocar 31 into the port. To be specific, in a state in which a needle-shaped obturator is inserted through the trocar 31, the operator inserts the trocar 31 into the abdominal wall 41 by inserting the obturator at the position of the port. The trocar 31 may have a small diameter so as to be minimally invasive. To be specific, the diameter of the trocar 31 may be smaller than or equal to 3 mm. After at least one of the trocars 32a to 32c and the trocar 31 has been inserted, the operator feeds a gas into the body through the trocar to inflate the body cavity to form a space in which devices are to be inserted.

Figure 4B:
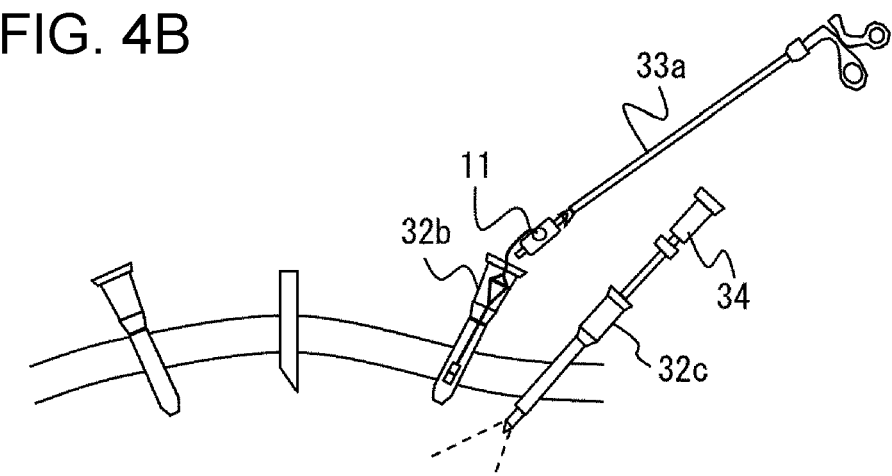

Next, as illustrated in FIG. 4B, the operator inserts an endoscope 34 into the body cavity through the trocar 32c and performs the following operations while observing the inside of the body by using the endoscope 34. The operator inserts the camera unit 11, which is held by forceps 33a; the camera-side cable 12; the camera support pipe 13; and the connector unit 100 into the body cavity through the trocar 32b. At this time, the connector cap 5 is attached to the camera-side cable connector 15a.

Figure 4C:
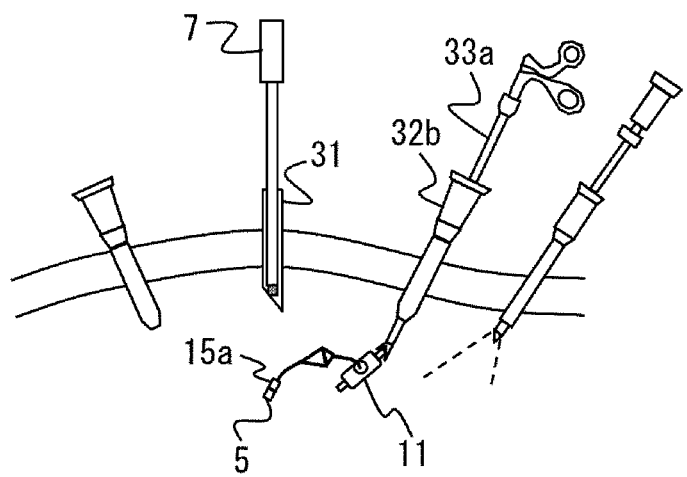

Next, as illustrated in FIG. 4C, the operator moves the camera unit 11 to a position near the trocar 31 by operating the forceps 33a, and inserts a setting jig 7 into the body cavity through the trocar 31.

Figure 4D:
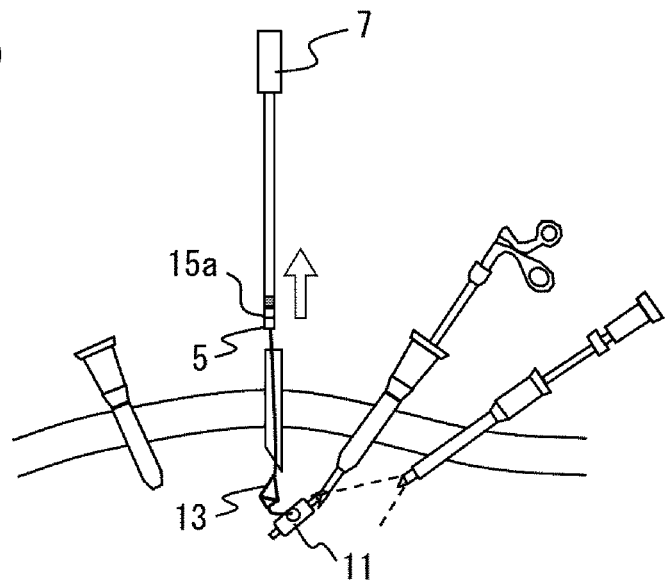

Next, as illustrated in FIG. 4D, the operator connects the setting jig 7 and the connector unit 100 to each other and pulls the camera-side cable 12 out of the body. The operator may use forceps or the like to pull the camera-side cable 12 out of the body.

Figure 4E:
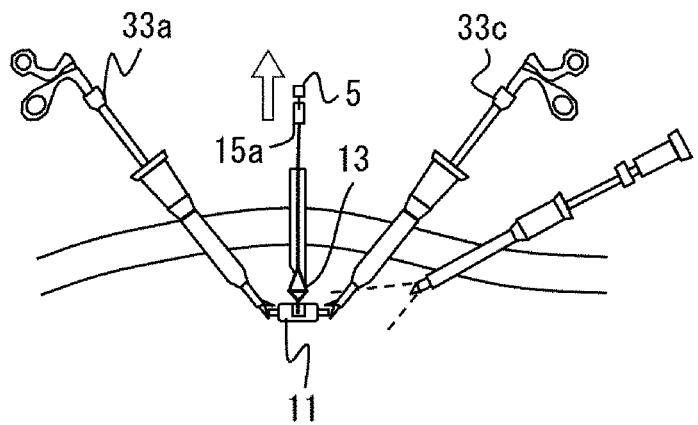
Figure 4F:
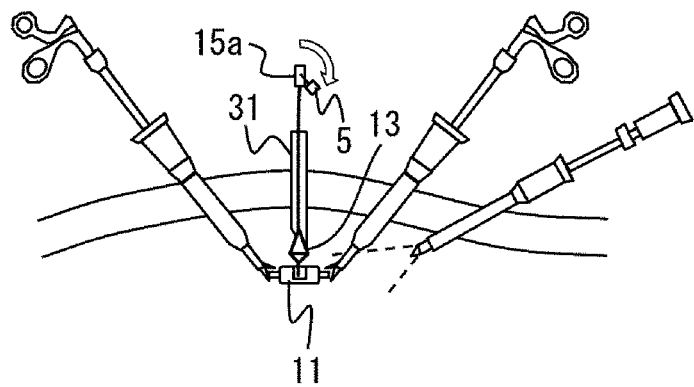

Next, as illustrated in FIG. 4E, the operator removes the connector cap 5 from the distal end portion 153 of the camera-side cable connector 15a by sliding the connector cap 5 in a direction away from the camera-side cable connector 15a. Next, as illustrated in FIG. 4F, the operator rotates the connector cap 5 to hold the connector cap 5 at a predetermined position relative to the camera-side cable connector 15a.

After the camera unit 11 has been set in the body, as illustrated in FIG. 3, the operator connects the camera-side cable 12 and the device-side cable 16 to each other by fitting the camera-side cable connector 15a into the device-side cable connector 15b. Thus, a local image of an affected portion is displayed on a display 118 by an endoscope controller 117. The entire image of the inside of an organ 42 captured by the camera unit 11 is displayed on the display 18 by the camera unit controller 17.

Figure 5A:
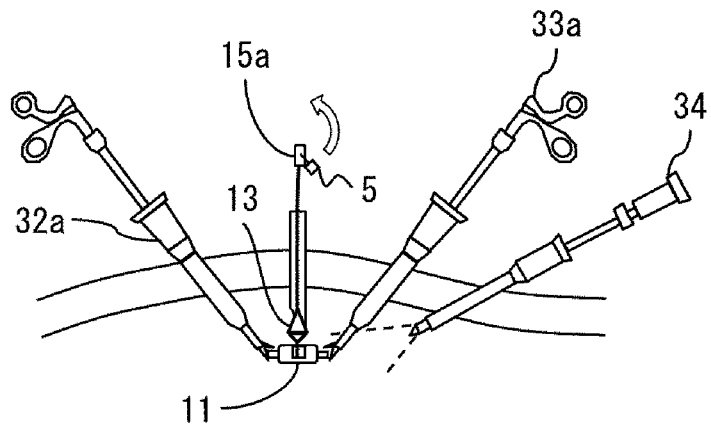
FIGS. 5A to 5E are schematic views illustrating an example of a method of removing the camera unit according to the first embodiment of the present disclosure out of the body.
Figure 5B:
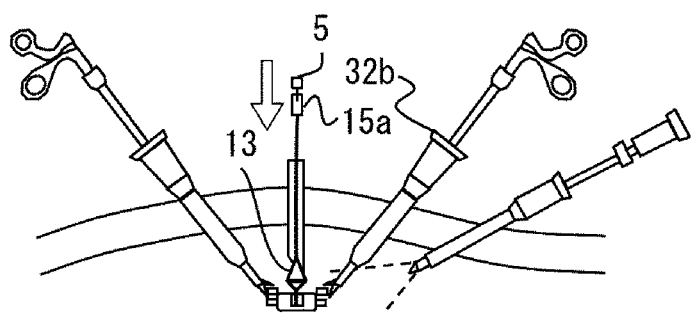
Figure 5C:
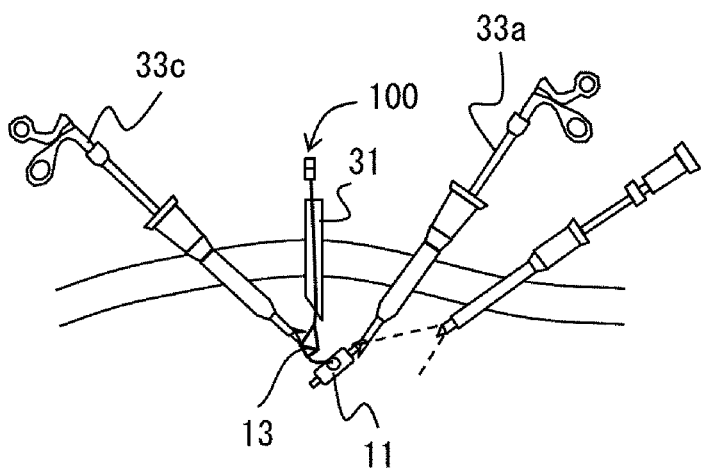
Figure 5D:
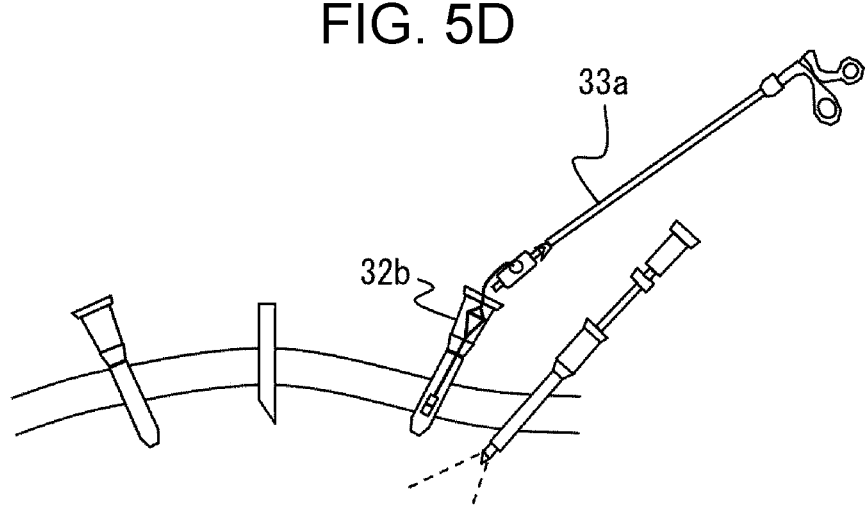
Figure 5E:
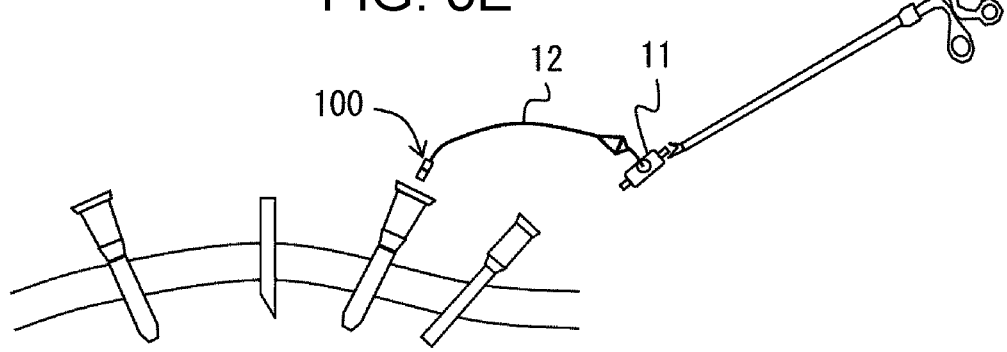

Next, details of a method of removing the camera unit 11 out of a body will be described. FIGS. 5A to 5E are schematic views illustrating an example of the method of removing the camera unit 11 out of the body. First, as illustrated in FIG. 5A, an operator rotates the connector cap 5, which is held at a predetermined position relative to the camera-side cable connector 15a. Next, as illustrated in FIG. 5B, the operator attaches the connector cap 5 to the distal end portion 153 of the camera-side cable connector 15a by sliding the connector cap 5 toward the camera-side cable connector 15a. Then, as illustrated in FIG. 5C, while holding the camera unit 11 with the forceps 33a, the operator inserts forceps 33c into a space between the camera support pipe 13 and the camera unit 11, and separates the camera support pipe 13 and the camera unit 11 from each other by operating the forceps 33c. Next, as illustrated in FIGS. 5D and 5E, the operator separates the camera support pipe 13 from the camera unit 11, and takes the camera unit 11, the camera-side cable 12, the camera support pipe 13, and the connector unit 100 out of the body through the trocar 32b. At this time, the camera-side cable 12 and the connector unit 100 are temporarily returned into the body through the trocar 31 and then pulled out of the body through the trocar 32b.

Second Embodiment

Figure 6C:
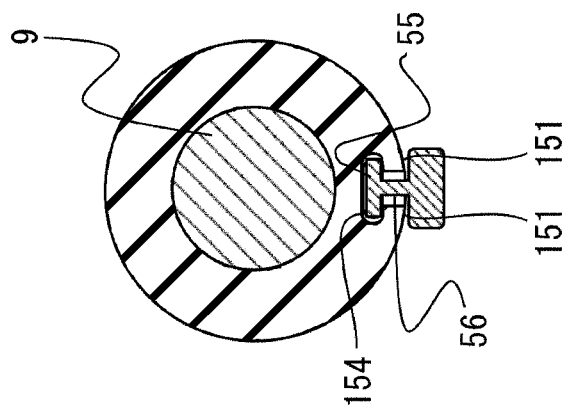
FIGS. 6A to 6C are perspective views of an example of a connector unit according to a second embodiment of the present disclosure.
Figure 6B:
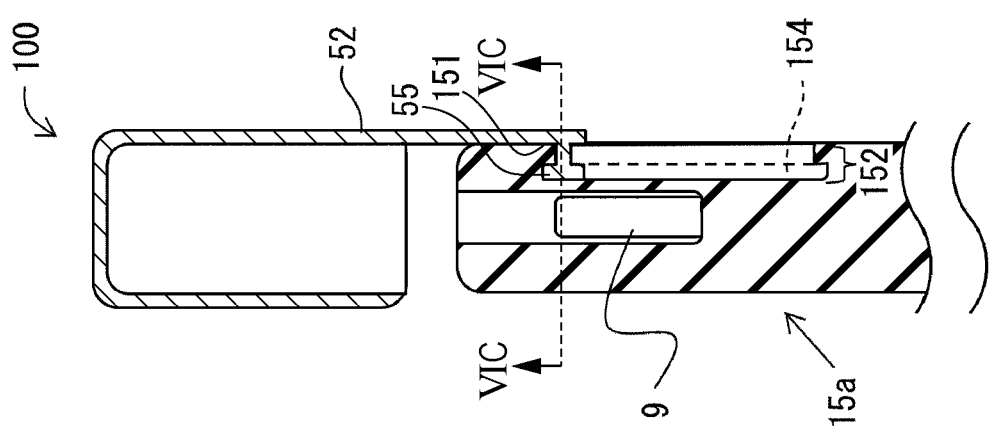
Figure 6A:
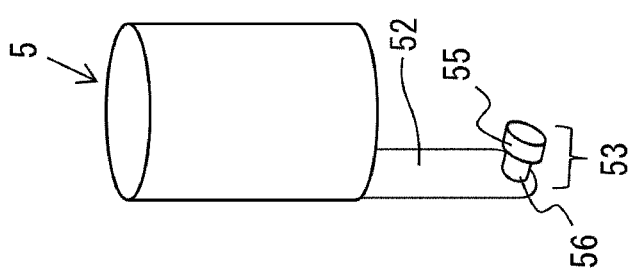

A second embodiment of the present disclosure will be described below. For convenience of description, members having the same functions as those described in the above embodiment will be denoted by the same numerals and the descriptions of such elements will not be repeated.
Overview In the present embodiment, a second groove 154 (second concave portion) is formed in a bottom part of the first groove 152 of the camera-side cable connector 15a, and the protruding section 53 of the connector cap 5 includes an engagement section 55, which is engageable with the second groove 154, at a distal end thereof.
Camera-Side Cable Connector 15a FIGS. 6A to 6C are perspective views of an example of the connector unit 100 according to the present embodiment. FIG. 6B is a sectional view taken along the central axis of the connector unit 100. As illustrated in FIG. 6B, the second groove 154 is formed in the bottom part of the first groove 152 of the camera-side cable connector 15a so as to jut out from a periphery of the bottom part of the first groove 152. In other words, the width of the first groove 152 is smaller than the width of the second groove 154.
Connector Cap 5

FIG. 6A is a perspective view of the connector cap 5. As illustrated in FIG. 6A, the protruding section 53 of the connector cap 5 includes the engagement section 55 at a distal end thereof. The outside diameter of the engagement section 55 is larger than the outside diameter of a slide shaft 56.

FIG. 6C is a sectional view taken along a dotted line VIC-VIC shown in FIG. 6B. As illustrated in FIG. 6C, the engagement section 55 engages with the second groove 154 of the camera-side cable connector 15a. To be specific, the engagement section 55 is formed so as to be fitted into the second groove 154.

As illustrated in FIG. 6A, in the present embodiment, the connector cap 5 includes one connection portion 52. As described above, the width of the first groove 152 of the camera-side cable connector 15a is smaller than the width of the second groove 154. In a cross section parallel to the bottom surface of the first groove, the diameter of the engagement section 55 is larger than the width of the first groove 152.

Therefore, as illustrated in FIGS. 6B and 6C, the engagement section 55 and the connection portion 52 of the connector cap 5 hold a part of the side wall 151 of the camera-side cable connector 15a near the first groove 152 therebetween. Accordingly, even though the number of the connection portion 52 is one and another connection portion 52 that faces the connection portion 52 is not present, the connector cap 5 is held by the camera-side cable connector 15a. The structure of the protruding section 53 including the engagement section 55 may be applied to the connector cap 5 according to the first embodiment, which has two connection portions 52.

With the structure described above, because the engagement section 55 engages with the second groove 154, compared with a structure that does not have the second groove and the engagement section, the protruding section 53 is not easily detached from the first groove 152. Therefore, it is possible to effectively prevent the connector cap 5 from becoming separated from the camera-side cable connector 15a and lost.
Operation of Removing Connector Cap 5 from Distal End Portion of Camera-Side Cable Connector 15a FIGS. 7A to 7D are schematic views illustrating an example of an operation of removing the connector cap 5 from the distal end portion of the camera-side cable connector 15a. A user moves (slides) the connector cap 5 in a direction away from the camera-side cable connector 15a so that the state of the connector cap 5 changes from a state shown in FIG. 7A to a state shown in FIG. 7B. Due to the user's operation, the connector cap 5 is removed from the distal end portion 153 of the camera-side cable connector 15a. Next, the user rotates the connector cap 5 relative to the camera-side cable connector 15a so that the state of the connector cap 5 changes from a state shown in FIG. 7B to a state shown in FIG. 7C. Due to the user's operation, the protruding section 53 rotates in the first groove 152. Moreover, the user slides the position of the connector cap 5 toward the proximal end of the camera-side cable connector 15a, for example, to an end of the first groove 152 so that the state of the connector cap 5 changes from a state shown in FIG. 7C to a state shown in FIG. 7D. Due to the user's operation, the position of the connector cap 5 can be moved to a predetermined position relative to the camera-side cable connector 15a.

Third Embodiment

A third embodiment of the present disclosure will be described below. For convenience of description, members having the same functions as those described in the above embodiments will be denoted by the same numerals and the descriptions of such elements will not be repeated. A connector cap 5 according to the present embodiment, which is the same as the connector cap 5 according to the first embodiment, will not be described here in detail.
Overview In the present embodiment, bottom surfaces of the first grooves 152 of the camera-side cable connector 15a include first convex portions 155 (first protruding structure) for fixing the protruding section 53 of the connector cap 5.
Camera-Side Cable Connector 15a FIGS. 8A to 8E illustrate an example of the connector unit 100 according to the present embodiment. FIG. 8F illustrates a reference example of a connector unit compared with the present embodiment. To be specific, FIG. 8A is a sectional view of the connector unit 100 in a state in which the connector cap 5 is removed from the camera-side cable connector 15a, taken along the central axis of the connector unit 100. FIG. 8B is a front view of the connector unit 100 in a state in which the connector cap 5 is removed from the camera-side cable connector 15a, as seen in the direction in which the first groove 152 is formed. FIG. 8C is a sectional view of the connector unit 100 in a state in which the connector cap 5 is attached to the camera-side cable connector 15a, taken along the central axis of the connector unit 100. FIG. 8D is a front view of the connector unit 100 in a state in which the connector cap 5 is attached to the camera-side cable connector 15a, as seen in the direction in which the first groove 152 is formed. FIG. 8E is a front view of the connector unit 100 in a state in which the connector cap 5 is removed from the camera-side cable connector 15a and is held at a predetermined position, as seen in the direction in which the first groove 152 is formed. In the present embodiment, as in the first embodiment, the camera-side cable connector 15a has two first grooves 152 that face each other with the central axis of the camera-side cable connector 15a therebetween.

As illustrated in FIGS. 8A and 8B, bottom surfaces 156 of the first grooves 152 of the camera-side cable connector 15a include the first convex portions 155, which are outwardly convex. As illustrated in FIG. 8C, in a state in which the connector cap 5 is attached to the camera-side cable connector 15a, the first convex portions 155 and first side surfaces 157 of the first grooves 152 hold the protruding sections 53 therebetween, the first side surfaces 157 being opposite to the distal end of the camera-side cable connector 15a.

As illustrated in FIG. 8A, the height of each of the first convex portions 155 from the bottom surface 156 may increase with decreasing distance from the first side surface 157. The first convex portion 155 may have an inverted V shape.

With the structure described above, in a state in which the connector cap 5 is attached to the camera-side cable connector 15a, the first convex portions 155 and the first side surfaces 157 hold the protruding sections 53 therebetween. For example, the first convex portions 155 may be appropriately adjusted so that the protruding sections 53 can be positioned between the first convex portions 155 and the first side surfaces 157 when the connector cap 5 is attached to the camera-side cable connector 15a. With this structure, in a state in which the connector cap 5 is attached to the camera-side cable connector 15a, even if the connector cap 5 starts to slide toward the distal end of the camera-side cable connector 15a, the protruding sections 53 engage with the first convex portions 155. The protruding sections 53 may be configured to slide over the first convex portions 155 if a force having a predetermined strength or more is applied to the connector cap 5 in a sliding direction along the first side surfaces 157. Therefore, sliding of the protruding sections 53 toward the distal end of the camera-side cable connector 15a unintended by a user can be prevented. Therefore, for example, compared with a structure illustrated in FIG. 8F, which does not have the first convex portions 155, removal of the connector cap 5 from the camera-side cable connector 15a unintended by a user can be effectively prevented. The arrow shown in FIG. 8F indicates the sliding direction of the protruding sections 53.

Therefore, for example, in the process of pulling the camera-side cable 12 out of the body as described in "Method of setting Camera Unit 11 in Body" in the first embodiment, removal of the connector cap 5 from the camera-side cable connector 15a can be prevented.

Moreover, because the first convex portions 155 and the first side surfaces 157 hold the protruding sections 53 therebetween, the connector cap 5 can be stably attached to the camera-side cable connector 15a.

Fourth Embodiment

A fourth embodiment of the present disclosure will be described below. For convenience of description, members having the same functions as those described in the above embodiments will be denoted by the same numerals and the descriptions of such elements will not be repeated. A connector cap 5 according to the present embodiment, which is the same as the connector cap 5 according to the first embodiment, will not be described here in detail.

Overview

In the present embodiment, third grooves 158 (third concave portion), which extend in circumferential direction of the camera-side cable connector 15a, are coupled to ends of the first grooves 152 opposite to the distal end portion 153 of the camera-side cable connector 15a.

Camera-Side Cable Connector 15a

Figures 9A, 9B, 9C, 9D:
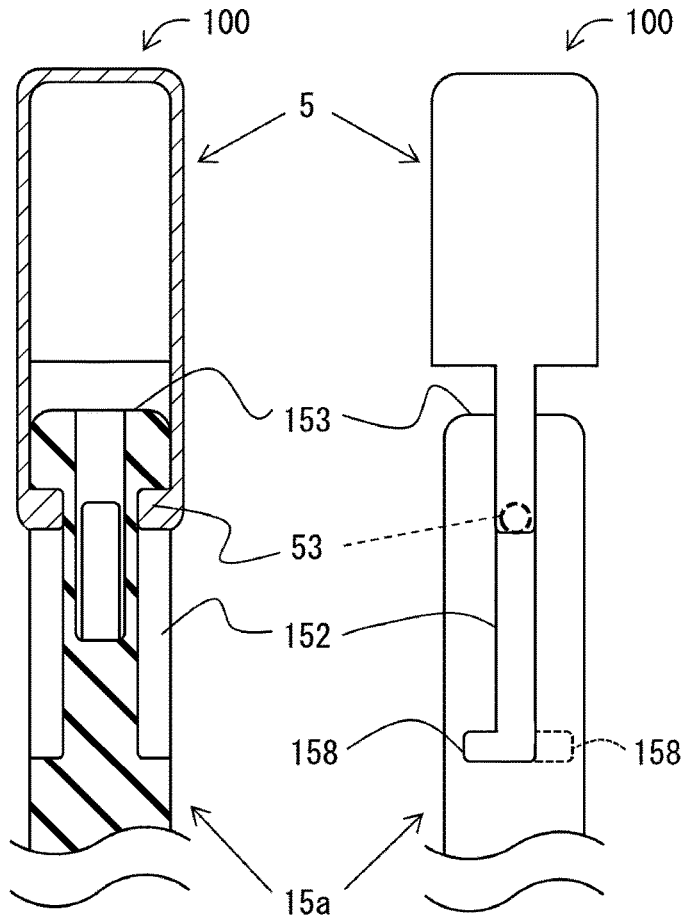
FIGS. 9A to 9D illustrate an example of a connector unit according to a fourth embodiment of the present disclosure.

FIGS. 9A to 9D illustrate an example of the connector unit 100 according to the present embodiment. To be specific, FIG. 9A is a sectional view of the connector unit 100 in a state in which the connector cap 5 is removed from the camera-side cable connector 15a, taken along the central axis of the connector unit 100. FIG. 9B is a front view of the connector unit 100 in a state in which the connector cap 5 is removed from the camera-side cable connector 15a, as seen in the direction in which the first groove 152 is formed. FIG. 9C is a front view of the connector unit 100 in a state in which the connector cap 5 is attached to the camera-side cable connector 15a, as seen in the direction in which the first groove 152 is formed. FIG. 9D is a front view of the connector unit 100 in a state in which the connector cap 5 is removed from the camera-side cable connector 15a and the protruding section 53 is disposed in the third groove 158, as seen in the direction in which the first groove 152 is formed. In the present embodiment, as in the first embodiment, the camera-side cable connector 15a has two first grooves 152 that face each other with the central axis of the camera-side cable connector 15a therebetween.

As illustrated in FIGS. 9B and 9C, the third grooves 158, which extend in circumferential direction of the camera-side cable connector 15a, are formed at ends of the first grooves 152 opposite to the distal end of the camera-side cable connector 15a. The third grooves 158 communicate with the first grooves 152. The protruding sections 53 are disposed so as to be movable also in the third grooves 158.

In FIG. 9B, one of the third grooves 158 is shown by a broken line. The third groove 158 is formed at a position facing a corresponding one of the first grooves 152, which is shown by solid lines in FIG. 9B, with the central axis therebetween and communicates with the first groove 152. That is, the third grooves 158 each communicate with a corresponding one of the two first grooves 152.

With the structure described above, for example, from a state in which the connector cap 5 is attached to the camera-side cable connector 15a, it is possible to slide the protruding sections 53 in the circumferential direction of the camera-side cable connector 15a and to dispose the protruding sections 53 in the third grooves 158. Accordingly, when the protruding sections 53 are disposed in the third grooves 158, even if the connector cap 5 starts to slide toward the distal end of the camera-side cable connector 15a, the protruding sections 53 engage with side walls of the third grooves 158. Therefore, sliding of the protruding sections 53 toward the distal end of the camera-side cable connector 15a unintended by a user can be prevented. Thus, compared with a structure that does not have the third grooves 158, removal of the connector cap 5 from the camera-side cable connector 15a unintended by a user can be effectively prevented. Moreover, by disposing the protruding sections 53 in the third grooves 158, the connector cap 5 can be stably attached to the camera-side cable connector 15a.

FIG. 9C illustrates a state in which the connector cap 5 is attached to the camera-side cable connector 15a. The arrow shown in FIG. 9C indicates a direction in which the connector cap 5 moves when the connector cap 5 is being attached to the camera-side cable connector 15a. As illustrated in FIG. 9C, when the connector cap 5 is being attached to the camera-side cable connector 15a, the connector cap 5 is pushed in the axial direction of the camera-side cable connector 15a. FIG. 9D illustrates a state in which the protruding sections 53 are disposed in the third grooves 158. The arrow shown in FIG. 9D indicates a direction in which the connector cap 5 moves when disposing the protruding sections 53 in the third grooves 158. As illustrated in FIG. 9D, when disposing the protruding sections 53 in the third grooves 158, the connector cap 5 is slid in the circumferential direction of the camera-side cable connector 15a. When the protruding sections 53 are disposed in the third grooves 158, even if the connector cap 5 is pulled in the axial direction of the camera-side cable connector 15a, the connector cap 5 is not removed from the camera-side cable connector 15a. That is, the connector cap 5 is fixed in place.

Therefore, for example, in the process of pulling the camera-side cable 12 out of the body as described in "Method of setting Camera Unit 11 in Body" in the first embodiment, removal of the connector cap 5 from the camera-side cable connector 15a can be prevented.

Operation of removing Connector Cap 5 from Distal End Portion of Camera-Side Cable Connector 15a FIGS. 10A to 10E are schematic views illustrating an example of an operation of removing the connector cap 5 from a distal end portion of the camera-side cable connector 15a. For example, as shown by a solid-line arrow in FIG. 10A, a user slides the connector cap 5 in the circumferential direction of the camera-side cable connector 15a to move the protruding sections 53 from the third grooves 158 to the first grooves 152.

Next, the user moves (slides) the connector cap 5 in a direction away from the camera-side cable connector 15a so that the state of the connector cap 5 changes from a state shown in FIG. 10A to a state shown in FIG. 10B. Due to the user's operation, the connector cap 5 is removed from the distal end portion 153 of the camera-side cable connector 15a. Next, the user rotates the connector cap 5 so that the state of the connector cap 5 changes from a state shown in FIG. 10B to a state shown in FIG. 10C. Due to the user's operation, the protruding sections 53 rotate in the first grooves 152. Moreover, the user moves (slides) the connector cap 5 toward the proximal end of the camera-side cable connector 15a so that the state of the connector cap 5 changes from a state shown in FIG. 10C to a state shown in FIG. 10D. Due to the user's operation, the protruding sections 53 are positioned at ends of the first grooves 152, which communicate with the third grooves 158. Moreover, the user rotates the camera-side cable connector 15a in the circumferential direction of the camera-side cable connector 15a so that the state of the connector cap 5 changes from a state shown in FIG. 10D to a state shown in FIG. 10E. Due to the user's operation, the protruding sections 53 are positioned in the third grooves 158, and the connector cap 5 is fixed in place.

First Modification

Figures 9E, 9F:
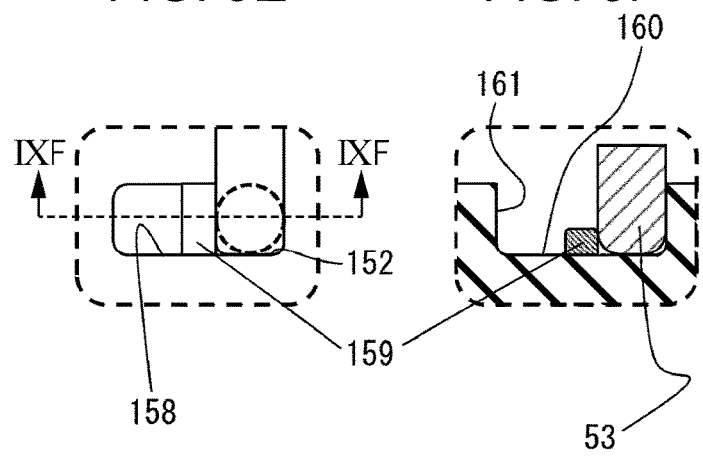
FIGS. 9E and 9F illustrate an example of a third groove according to a modification of the fourth embodiment of the present disclosure.

Referring to FIGS. 9E and 9F, a modification of the present embodiment will be described. In the present modification, a third convex portion 159, for fixing the protruding section 53, is disposed in the third groove 158.

FIGS. 9E and 9F illustrate an example of the third groove 158 according to the present modification. To be specific, FIG. 9E is an enlarged front view of the connector unit 100, as seen in a direction in which the first groove 152 and the third groove 158 are formed. FIG. 9F is a sectional view taken along a broken line IXF-IXF shown in FIG. 9E.

As illustrated in FIGS. 9E and 9F, the third convex portion 159, which is outwardly convex, is disposed on a bottom surface 160 of the third groove 158. When the protruding section 53 is positioned in the third groove 158, the third convex portion 159 and an end surface 161 of the third groove 158, which extends in the axial direction of the camera-side cable connector 15a, hold the protruding section 53 therebetween.

With the structure described above, in a state in which the connector cap 5 is attached to the camera-side cable connector 15a, it is possible to dispose the protruding sections 53 in the third grooves 158 by sliding the protruding sections 53 in the circumferential direction of the camera-side cable connector 15a. Moreover, the third convex portions 159 and the end surfaces 161 can hold the protruding sections 53 therebetween. For example, the protruding sections 53 may be configured to slide over the third convex portions 159 if a force having a predetermined strength or more is applied to the connector cap 5 in a direction along the third grooves 158.

Therefore, compared with a structure that does not have the third grooves 158 and the third convex portions 159, removal of the connector cap 5 from the camera-side cable connector 15a unintended by a user can be effectively prevented.

Moreover, because the third convex portions 159 and the end surfaces 161 hold the protruding sections 53 therebetween, the connector cap 5 can be stably attached to the camera-side cable connector 15a.

Second Modification

Figure 11A:
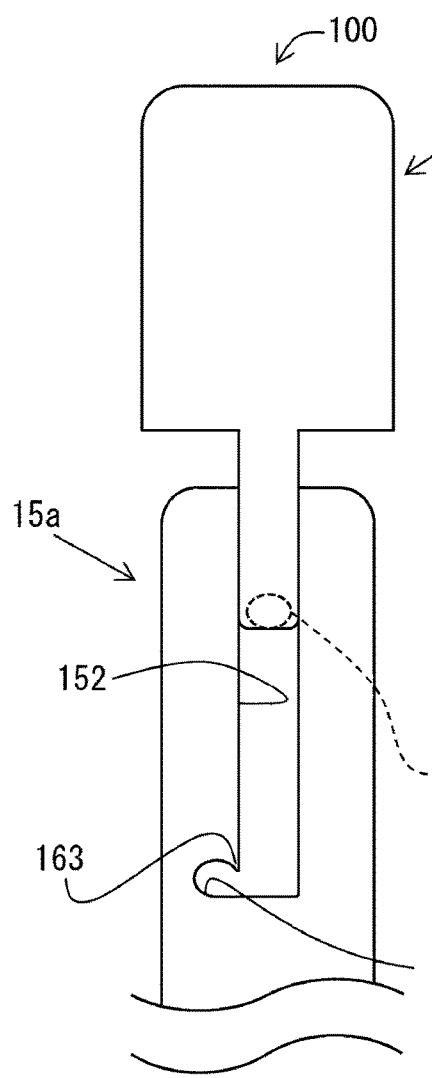
FIGS. 11A to 11C illustrate an example of a third groove according to another modification of the fourth embodiment of the present disclosure.
Figure 11B:
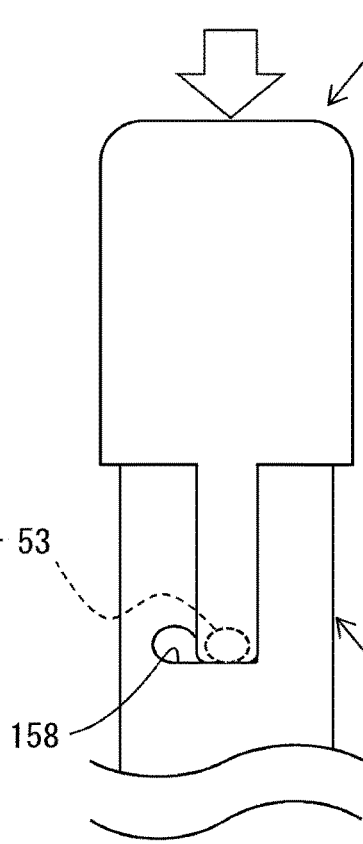
Figure 11C:
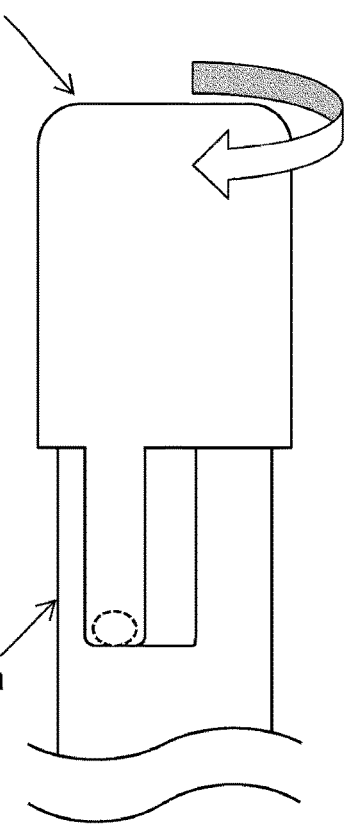

Referring to FIGS. 11A to 11C, a second modification according to the present embodiment will be described. In the present modification, the width of the third groove 158 decreases with decreasing distance to a connection region (coupling region) where the third groove 158 and the first groove 152 are connected to each other.

Structure of Third Groove 158

FIGS. 11A to 11C illustrate an example of the third groove 158 according to the present modification. To be specific, FIGS. 11A to 11C are front views of the connector unit 100, as seen in a direction in which the first groove 152 and the third groove 158 are formed.

As illustrated in FIGS. 11A and 11B, for example, a part of a side surface of the third groove 158 may be formed as a fourth convex portion 163 that is convex toward the inside of the third groove 158.

FIG. 11A illustrates a state in which the connector cap 5 is removed from the camera-side cable connector 15a. FIG. 11B illustrates a state in which the connector cap 5 is attached to the camera-side cable connector 15a. The arrow shown in FIG. 11B indicates a direction in which the connector cap 5 moves when the connector cap 5 is being attached to the camera-side cable connector 15a. As illustrated in FIG. 11B, when the connector cap 5 is being attached to the camera-side cable connector 15a, the connector cap 5 is pushed in the axial direction of the camera-side cable connector 15a. FIG. 11C illustrates a state in which the protruding section 53 is disposed in the third groove 158. The arrow shown in FIG. 11C indicates a direction in which the connector cap 5 moves when the protruding section 53 is being disposed in the third groove 158. As illustrated in FIG. 11C, when disposing the protruding section 53 in the third groove 158, the connector cap 5 is slid in the circumferential direction of the camera-side cable connector 15a. As described above, the width of the third groove 158 decreases with decreasing distance to the connection region (coupling region) where the third groove 158 and the first groove 152 are connected to each other. Therefore, when the protruding section 53 is once disposed in the third groove 158, the protruding section 53 is not easily removed from the third groove 158. Therefore, removal of the connector cap 5 from the camera-side cable connector 15a unintended by a user can be effectively prevented.

Fifth Embodiment

A fifth embodiment of the present disclosure will be described below. For convenience of description, members having the same functions as those described in the above embodiments will be denoted by the same numerals and the descriptions of such elements will not be repeated. In particular, differences between the present embodiment and the second embodiment will be described.

The present embodiment has two second convex portions 166 (second protruding structure) that face side surfaces of the first groove 152.

Figure 12A:
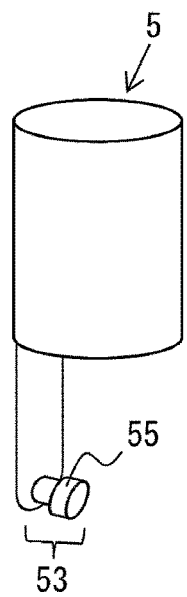

FIGS. 12A to 12E illustrate an example of the connector unit 100 according to the present embodiment. FIG. 12A is a perspective view of the connector cap 5. The structure of the connector cap 5 according to the present embodiment is the same as that of the connector cap 5 according to the second embodiment.

Figures 12B, 12C:
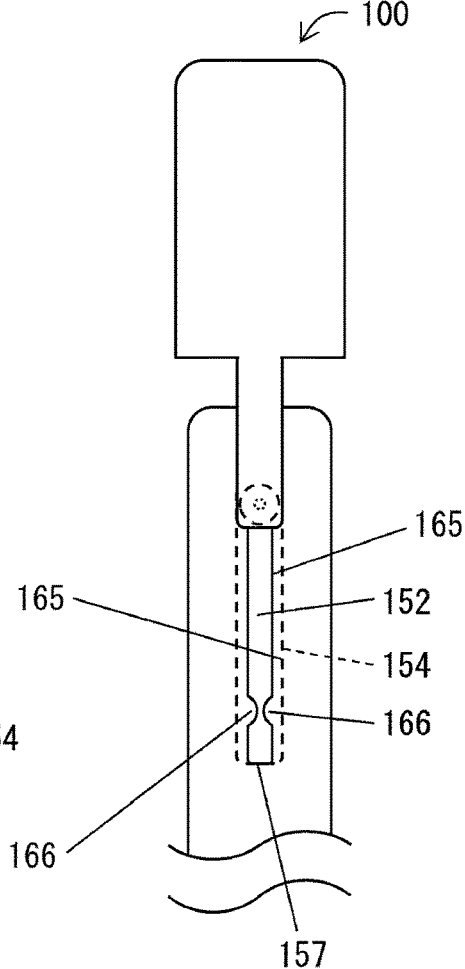

FIG. 12B is a sectional view taken along the central axis of the connector unit 100. FIG. 12C is a front view of the connector unit 100 in a state in which the connector cap 5 is removed from the camera-side cable connector 15a, as seen in the direction in which the first groove 152 is formed. FIG. 12D is a front view of the connector unit 100 in a state in which the connector cap 5 is attached to the camera-side cable connector 15a, as seen in the direction in which the first groove 152 is formed. FIG. 12E is a sectional view of the connector unit 100 in a state in which the connector cap 5 is attached to the camera-side cable connector 15a, taken along the central axis of the connector unit 100.

As illustrated in FIG. 12C, two second side surfaces 165 of the first groove 152 that extend in the axial direction of the camera-side cable connector 15a each include the second convex portion 166, which is convex toward a corresponding one of the second side surfaces 165 that the second convex portion 166 faces.

When the protruding section 53 is positioned between the second convex portions 166 and the first side surface 157, the two second convex portions 166 and the first side surface 157 hold the protruding section 53 therebetween.

With the structure described above, in a state in which the connector cap 5 is attached to the camera-side cable connector 15a, the two second convex portions 166 and the first side surface 157 hold the protruding section 53 therebetween. The positions of the second convex portions 166 are appropriately adjusted so that the protruding section 53 is positioned between the second convex portions 166 and the first side surface 157 when the connector cap 5 is attached to the camera-side cable connector 15a.

With this structure, when the connector cap 5 is attached to the camera-side cable connector 15a, even if the connector cap 5 starts to slide toward the distal end of the camera-side cable connector 15a, the protruding section 53 engages with the two second convex portions 166. For example, the protruding section 53 may be configured to slide over the second convex portions 166 if a force having a predetermined strength or more is applied to the connector cap 5 along the first groove 152. Therefore, sliding of the protruding section 53 toward the distal end of the camera-side cable connector 15a unintended by a user can be prevented. Thus, compared with a structure that does not have the second convex portions 166, removal of the connector cap 5 from the camera-side cable connector 15a unintended by a user can be effectively prevented.

Moreover, because the two second convex portions 166 and the first side surface 157 hold the protruding section 53 therebetween, the connector cap 5 can be stably attached to the camera-side cable connector 15a.

Sixth Embodiment

A sixth embodiment of the present disclosure will be described below. For convenience of description, members having the same functions as those described in the above embodiments will be denoted by the same numerals and the descriptions of such elements will not be repeated. In particular, differences between the present embodiment and the third embodiment will be described.

Overview

In the present embodiment, the shape of the protruding section 53 is a regular prism. In a state in which the connector cap 5 is not attached to the camera-side cable connector 15a, corners of the regular prism are engaged with the first convex portions 155. Therefore, the connector cap 5 can be held at predetermined angles relative to the camera-side cable connector 15a.

Camera-Side Cable Connector 15a

FIGS. 13A to 13F illustrate an example of the connector unit 100 according to the present embodiment. To be specific, FIG. 13A is a perspective view of an example of the connector cap 5 according to the present embodiment. FIG. 13B is a sectional view of the connector unit 100 in a state in which the connector cap 5 is removed from the camera-side cable connector 15a, taken along the central axis of the connector unit 100. FIG. 13C is a front view of the connector unit 100 in a state in which the connector cap 5 is removed from the camera-side cable connector 15a, as seen in the direction in which the first groove 152 is formed. The structure of the camera-side cable connector 15a according to the present embodiment is the same as that of the camera-side cable connector 15a according to the third embodiment.

Connector Cap 5

As illustrated in FIGS. 13A and 13C, the connector cap 5 according to the present embodiment includes the protruding section 53 whose shape is a regular triangular prism.

FIG. 13D is a front view of the connector unit 100 in a state in which the connector cap 5 is attached to the camera-side cable connector 15a, as seen in the direction in which the first groove 152 is formed. FIGS. 13E and 13F are front views of the connector unit 100 in a state in which the connector cap 5 is removed from the camera-side cable connector 15a and is held at predetermined positions, as seen in the direction in which the first groove 152 is formed.

As illustrated in FIGS. 13E and 13F, in a state in which the connector cap 5 is not attached to the camera-side cable connector 15a, the connector cap 5 is held at predetermined angles relative to the camera-side cable connector 15a. To be specific, because the corners of the protruding section 53 engage with the first convex portion 155, the connector cap 5 can be held at predetermined angles relative to the camera-side cable connector 15a. FIG. 13E illustrates an example in which the connector cap 5 is held at a predetermined angle of 60 degrees. FIG. 13F illustrates an example in which the connector cap 5 is held at a predetermined angle of 120 degrees.

FIGS. 14A to 14C illustrate examples of protruding sections 53 having other shapes. In the example illustrated in FIG. 14A, the connector cap 5 includes protruding sections 53 whose shape is a regular quadrangular prism. In the example illustrated in FIG. 14B, the connector cap 5 includes protruding sections 53 whose shape is a regular pentagonal prism. In the example illustrated in FIG. 14C, the connector cap 5 includes protruding sections 53 whose shape is a regular hexagonal prism. The shape of the protruding sections 53 is not particularly limited, as long as the shape is a regular prism.

Third Modification

Referring to FIG. 15A to 15C, a modification of the present embodiment will be described. The present modification includes a fitting structure 169 at an end of the first groove 152 near the proximal end of the camera-side cable connector 15a.

The fitting structure 169 has a shape corresponding to the shape of the protruding section 53 of the connector cap 5, which is a regular prism, so that the protruding section 53 can be fitted into the fitting structure 169. FIGS. 15A to 15C illustrate examples of the connector unit 100 according to the present modification. To be specific, FIGS. 15A to 15C are front views of the connector unit 100 in a state in which the connector cap 5 is removed from the camera-side cable connector 15a, as seen in the direction in which the first groove 152 is formed. In the example illustrated in FIG. 15A, the fitting structure 169 has a shape corresponding to the protruding section 53 whose shape is a regular triangular prism. In the example illustrated in FIG. 15B, the fitting structure 169 has a shape corresponding to the protruding section 53 whose shape is a regular quadrangular prism. In the example illustrated in FIG. 15C, the fitting structure 169 has a shape corresponding to the protruding section 53 whose shape is a regular hexagonal prism.

Fourth Modification

Referring to FIG. 15D, a modification of the present embodiment will be described. FIG. 15D illustrates an example of the protruding section 53 according to the present modification. To be specific, FIG. 15D is a front view of the connector unit 100 according to the present modification, as seen in the direction in which the first groove 152 is formed. As illustrated in FIG. 15D, the connector cap 5 includes the protruding section 53 having a gear-like shape. To be specific, the protruding section 53 has a gear-like shape in a cross section parallel to the bottom surface of the first groove 152. The camera-side cable connector 15a includes a projection 168 that is fitted into a space between teeth of the protruding section 53.

The protruding section 53 and the projection 168 may form a ratchet structure.

Seventh Embodiment

A seventh embodiment of the present disclosure will be described below. For convenience of description, members having the same functions as those described in the above embodiments will be denoted by the same numerals and the descriptions of such elements will not be repeated.

Connector Cap 5 and Setting Jig 7

In the first embodiment, an operation of connecting the setting jig 7 and the connector unit 100 to each other and an operation of pulling the camera-side cable 12 out of the body have been described in "Method of setting Camera Unit 11 in Body".

In the present embodiment, referring to FIGS. 16A to 16D, examples of the structure of the setting jig 7 for pulling the connector unit 100, which has been inserted into the body, out of the body and examples of the structure of the connector cap 5 that is connectable to the setting jig 7 will be described.

FIGS. 16A to 16D illustrate examples of the connector cap 5 and the setting jig 7.

Figure 16A:
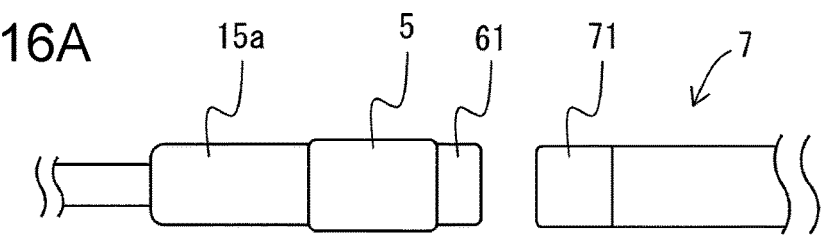
FIGS. 16A to 16D illustrate examples of a connector cap and a setting jig according to a seventh embodiment of the present disclosure.

In the example illustrated in FIG. 16A, the connector cap 5 includes a magnet portion 61 at a distal end thereof. The setting jig 7 includes a magnet portion 71 at a distal end thereof. The magnet portion 71 of the setting jig 7 and the magnet portion 61 of the connector cap 5 are magnetically connected to each other in the body.

Figure 16B:
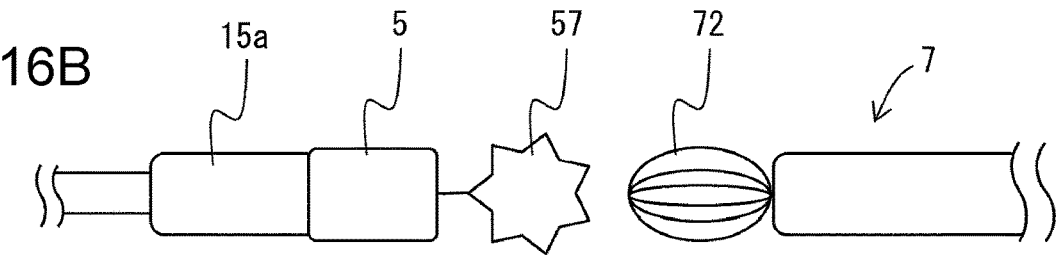

In the example illustrated in FIG. 16B, the connector cap 5 includes a latch 57 at a distal end thereof. The setting jig 7 includes a whisk-shaped end portion 72 at a distal end thereof. The whisk-shaped end portion 72 is composed of a plurality of curved holding wires that are connected to each other at two points as both ends thereof and that have an ellipsoidal shape (rotating elliptical shape). The plurality of holding wires can be deformed by applying an external force. The setting jig 7 may have a structure such that the whisk-shaped end portion 72 is pulled into a cylindrical tube via an end-portion-driving hard wire when a handle lever (not shown) is operated. When a force is not applied, the distal end of the whisk-shaped end portion 72 expands in a whisk shape and the distance between the holding wires increases. When the lever is pulled to apply a force that pulls this part into the cylindrical tube, the distance between the holding wires decreases. Thus, the distance between the holding wires of the whisk-shaped end portion 72 is variable. To be more specific, the distance between the holding wires when the whisk-shaped end portion 72 is positioned outside the cylindrical tube may be a distance corresponding to the diameter of the latch 57. Thus, when the whisk-shaped end portion 72 is pressed against the latch 57, the latch 57 can enter the inside of the whisk-shaped end portion 72, and movement of the latch 57 to the outside of the whisk-shaped end portion 72 can be suppressed.

Figure 16C:
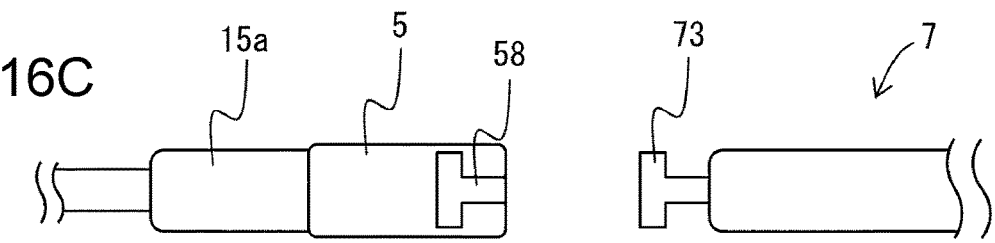

In the example illustrated in FIG. 16C, the connector cap 5 includes a second connection portion 58 at a distal end thereof. The setting jig 7 includes a fitting portion 73 at a distal end thereof. The second connection portion 58 of the connector cap 5 has a concave shape corresponding to the shape of the fitting portion 73 of the setting jig 7. By fitting the fitting portion 73 into the concave shape, the setting jig 7 and the connector cap 5 are connected to each other.

Figure 16D:
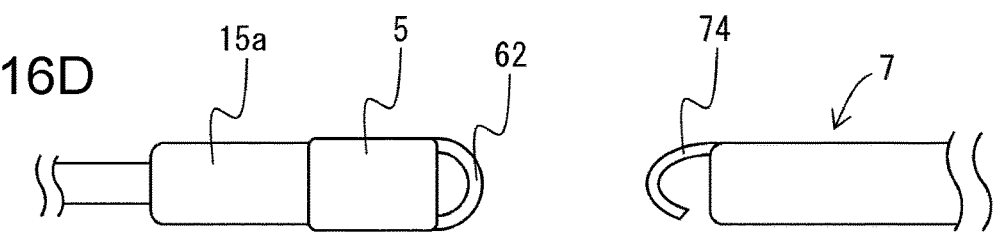

In the example illustrated in FIG. 16D, the connector cap 5 includes a hook receiving portion 62 at a distal end thereof. The setting jig 7 includes a hook 74 at a distal end thereof. By engaging the hook 74 of the setting jig 7 with the hook receiving portion 62 of the connector cap 5, the setting jig 7 and the connector cap 5 are connected to each other.

The strength of connection between the connector cap 5 and the camera-side cable connector 15a may be larger than the strength of connection between the setting jig 7 and the connector cap 5.

Eighth Embodiment

An eighth embodiment of the present disclosure will be described below. For convenience of description, members having the same functions as those described in the above embodiments will be denoted by the same numerals and the descriptions of such elements will not be repeated.

Overview

In the present embodiment, the connector cap 5 and the camera-side cable connector 15a are connected by a wire 8 and thereby integrated.

Wire 8

The wire 8 connects the connector cap 5 and the camera-side cable connector 15a. Referring to FIGS. 17A to 17E, variations of a method of connecting the connector cap 5 and the camera-side cable connector 15a will be described.

FIGS. 17A to 17D illustrate examples of a method of connecting the connector cap 5 and the camera-side cable connector 15a. The left figures each illustrate a state in which the connector cap 5 is removed from the camera-side cable connector 15a. The right figures each illustrate a state in which the connector cap 5 is attached to the camera-side cable connector 15a.

Figure 17A:
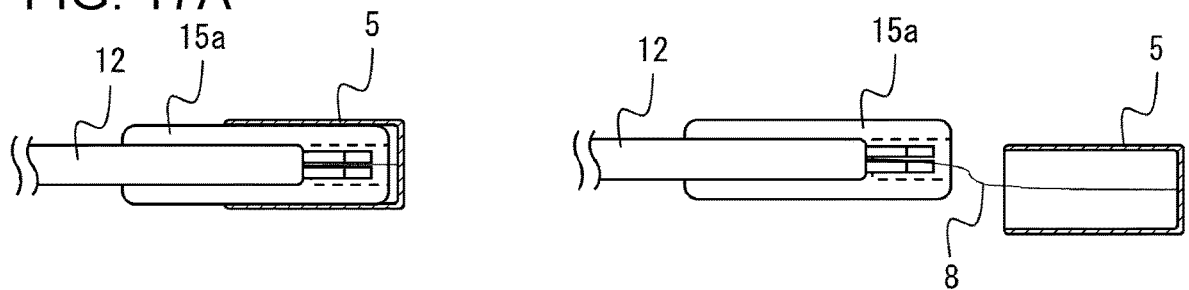
FIGS. 17A to 17E illustrate examples of a method of connecting a connector cap and a camera-side cable connector according to an eighth embodiment of the present disclosure.

In the example illustrated in FIG. 17A, the wire 8 and the connector cap 5 are connected to each other at substantially the center of the connector cap 5. The wire 8 and the camera-side cable connector 15a are connected to each other at substantially the center of the camera-side cable connector 15a.

Figure 17B:
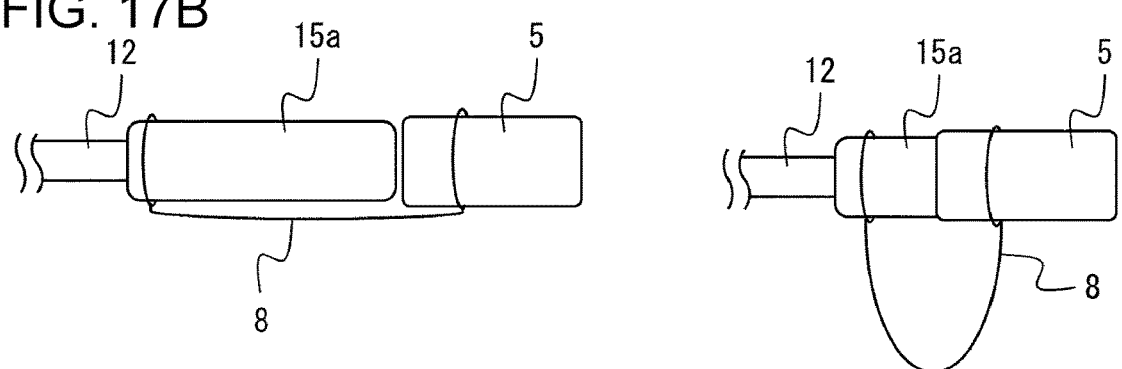

In the example illustrated in FIG. 17B, the wire 8 and the connector cap 5 are connected to each other by winding the wire 8 around the connector cap 5. The wire 8 and the camera-side cable connector 15a are connected to each other by winding the wire 8 around the camera-side cable connector 15a.

Figure 17C:
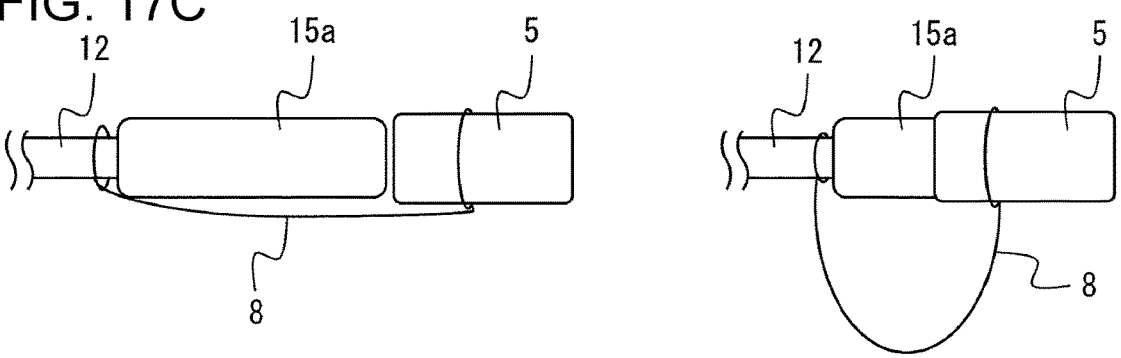

In the example illustrated in FIG. 17C, the wire 8 and the connector cap 5 are connected to each other by winding the wire 8 around the connector cap 5. The wire 8 and the camera-side cable 12 are connected to each other by winding the wire 8 around the camera-side cable 12.

The camera-side cable connector 15a is positioned at the distal end of the camera-side cable 12, and the outside diameter of the camera-side cable connector 15a is larger than the outside diameter of the camera-side cable 12. Thus, with the structure described above, removal of the wire 8 can be suppressed.

Figure 17D:
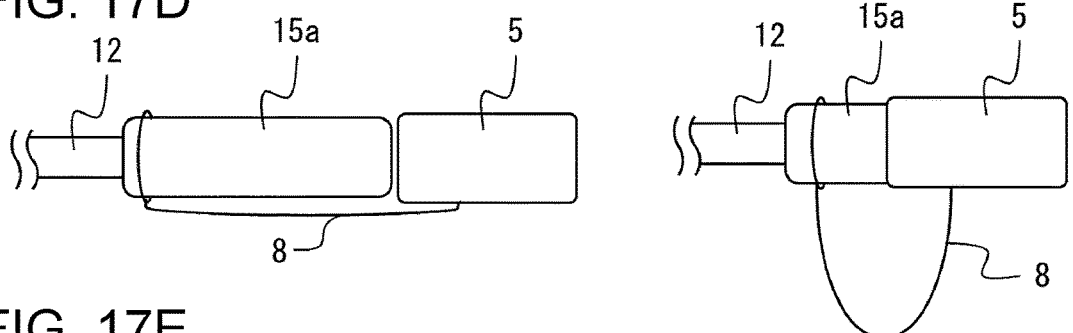
Figure 17E:
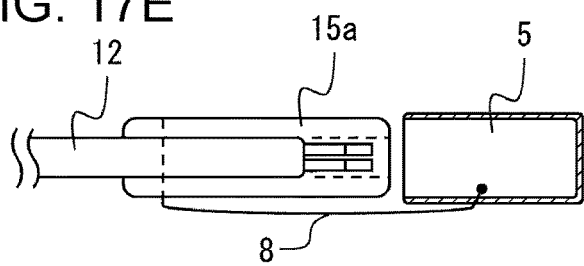

FIG. 17E is a sectional view of the connector unit illustrated in FIG. 17D. In the example illustrated in FIGS. 17D and 17E, the wire 8 extends through a side surface of the connector cap 5 and is connected to the connector cap 5 at a position inside the connector cap 5. The wire 8 and the camera-side cable connector 15a are connected to each other by winding the wire 8 around the camera-side cable connector 15a. Alternatively, the wire 8 may extend through a side surface of the camera-side cable 12, and may be connected to the camera-side cable 12 at a position inside the camera-side cable 12.

Grooves may be formed in a side surface of the camera-side cable connector 15a and a side surface of the connector cap 5 where the wire 8 is to be wound.

A groove may be formed in a side surface of the camera-side cable connector 15a so as to extend in the axial direction of the camera-side cable connector 15a. The groove may be used to accommodate the wire 8.

With the structure described above, increase in the outside diameter of the connector unit, which is composed of the connector cap 5 and the camera-side cable connector 15a, can be suppressed. Therefore, the connector unit can be inserted into the body by using a trocar having a small diameter.

The length of the connector cap 5 may be smaller than the diameter of a trocar that is used to insert a camera unit into the body and larger than the diameter of other trocars.

When the connector cap 5 has a sufficient length, the probability of falling of the connector cap into a trocar and into a body can be reduced.

SUMMARY

A connector unit (100) according to a first aspect of the present disclosure includes a connector (camera-side cable connector 15a), and a tubular connector cap (5) that is removably attached to the connector and whose distal end is closed. The connector cap includes a connection portion (52) at an end adjacent to an opening thereof, and the connection portion movably connects the connector cap to the connector. The connection portion is movably connected to the connector in a state in which a concave portion (first groove 152, first groove 59) included in one of a side wall of the connector and the connection portion and a convex portion (protruding section 53, protruding section 170) included in the other of the side wall and the connection portion are fitted to each other. In a state in which the connector cap is attached to the connector, a distal end portion of the connector is inserted from the opening into a space (54) in the connector cap.

With the structure described above, because the convex portion is movably disposed in the concave portion, the convex portion can be moved in the axial direction of the connector in the concave portion, or the convex portion can be rotated in the concave portion. Accordingly, it is possible to attach the connector cap, which couples the convex portion and the connection portion, to the connector and to remove the connector cap from the connector by displacing the connector cap relative to the connector in the axial direction or by rotating the connector cap around the convex portion as a rotation axis. Therefore, this structure has an advantage in that it is possible to, by integrating the connector and the connector cap, easily attach the connector cap to the connector and remove the connector cap from the connector while preventing the connector cap from becoming lost and from being forgotten to be attached to the connector.

With the structure described above, when the connector cap is attached to the connector, the distal end portion of the connector is covered by the connector cap. Accordingly, for example, compared with a connector cap that is structured to cover only the opening at the distal end of the connector, the connector cap can be stably attached and can shield a larger area at the distal end of the connector from the outside. Therefore, this structure has an advantage in that it is possible to effectively prevent, for example, the following: unintended removal of the connector cap from the connector; and image blur or the like that may occur due to poor connection or short circuit when a bodily fluid, a body tissue, or the like adheres to a terminal at the distal end of the connector.

In the present specification, the term "removal" refers to separation of the connector cap from the distal end portion of the connector while maintaining a state in which the connector cap is removably attached to the distal end portion of the connector.

In a connector unit according to a second aspect of the present disclosure, the concave portion may be included in the side wall (151) of the connector, may extend in an axial direction in which a central axis of the connector extends, and may open outward; and the convex portion may be included in the connection portion, may protrude toward the central axis, and may be movably disposed in the concave portion.

With the structure described above, because the convex portion of the connection portion is movably disposed in the concave portion of the side wall of the connector, the convex portion of the connection portion can be moved in the axial direction of the connector in the concave portion of the side wall of the connector, or the convex portion can be rotated in the concave portion of the side wall of the connector.

A connector unit according to a third aspect of the present disclosure is the connector unit according to the first or second aspect, in which a second concave portion (second groove 154) may be formed in a bottom part of the concave portion so as to jut out from a periphery of the bottom part, and the convex portion may include an engagement section (55), which engages with the second concave portion, at a distal end thereof.

With the structure described above, because the engagement section engages with the second concave portion, compared with a structure that does not have the second concave portion and the engagement section, the convex portion is not easily detached from the concave portion. Therefore, this structure has an advantage in that it is possible to effectively prevent the connector cap from becoming separated from the connector and lost.

A connector unit according to a fourth aspect of the present disclosure is the connector unit according to any one of the first to third aspects, in which a bottom surface (156) of the concave portion may include a first protruding structure (first convex portion 155) that is outwardly convex, and, in a state in which the connector cap is attached to the connector, the first protruding structure and a first side surface (157) of the concave portion may hold the convex portion therebetween, the first end surface being opposite to a distal end of the connector.

With the structure described above, in a state in which the connector cap is attached to the connector, the first protruding structure and the first side surface hold the convex portion therebetween. Accordingly, in a state in which the connector cap is attached to the connector, even if the connector cap starts to slide toward the distal end of the connector, the convex portion engages with the first protruding structure. Therefore, sliding of the convex portion toward the distal end of the connector unintended by a user can be prevented. Therefore, this structure has an advantage in that, compared with a structure that does not have the first protruding structure, removal of the connector cap from the connector unintended by a user can be effectively prevented.

Moreover, this structure has an advantage in that, because the first protruding structure and the first side surface hold the convex portion therebetween, the connector cap can be stably attached to the connector.

A connector unit according to a fifth aspect of the present disclosure is the connector unit according to any one of the first to fourth aspects, in which a third concave portion (third groove 158) may be formed at an end of the concave portion, the end being opposite to a distal end of the connector, and the third concave portion extends in a circumferential direction of the connector and communicates with the concave portion; and the convex portion may be disposed so as to be movable also in the third concave portion.

With the structure described above, in a state in which the connector cap is attached to the connector, it is possible to further slide the convex portion in the circumferential direction of the connector and to dispose the convex portion in the third concave portion. Accordingly, when the convex portion is disposed in the third concave portion, even if the connector cap starts to slide toward the distal end of the connector, the convex portion engages with a side wall of the third concave portion. Therefore, sliding of the convex portion toward the distal end of the connector unintended by a user can be prevented. Thus, this structure has an advantage in that, compared with a structure that does not have the third concave portion, removal of the connector cap from the connector unintended by a user can be effectively prevented.

Moreover, this structure has an advantage in that, by disposing the convex portion in the third concave portion, the connector cap can be stably attached to the connector.

A connector unit according to a sixth aspect of the present disclosure is the connector unit according to the fifth aspect, in which a protruding structure (third convex portion 159) that is outwardly convex may be disposed on a bottom surface (160) of the third concave portion; and, when the convex portion is positioned in the third concave portion, the protruding structure and an end surface of the third concave portion may hold the convex portion therebetween, the end surface extending in a direction in which a central axis of the connector extends.

With the structure described above, in a state in which the connector cap is attached to the connector, it is possible to dispose the convex portion in the third concave portion by sliding the convex portion in the circumferential direction of the connector. Moreover, the protruding structure and the end surface can hold the convex portion, which is disposed in the third concave portion, therebetween. Therefore, this structure has an advantage in that, compared with a structure that does not have the third concave portion and the protruding structure, removal of the connector cap from the connector unintended by a user can be effectively prevented.

Moreover, this structure has an advantage in that, because the protruding structure and the end surface hold the convex portion therebetween, the connector cap can be stably attached to the connector.

A connector unit according to a seventh aspect of the present disclosure is the connector unit according to any one of the second to sixth aspects, in which two second side surfaces (165) of the concave portion that extend in the axial direction of the connector may each include a second protruding structure (second convex portion 166) that is convex toward a corresponding one of the second side surfaces that the second protruding structure faces; and, when the convex portion is positioned between the second protruding structures and a first side surface of the concave portion, the first side surface being opposite to a distal end of the connector, the two second protruding structures and the first side surface may hold the convex portion therebetween.

With the structure described above, in a state in which the connector cap is attached to the connector, the two second protruding structures and the first side surface hold the convex portion therebetween. For example, when the connector cap is attached to the connector, the convex portion may be positioned between the second protruding structures and the first side surface. With this structure, when the connector cap is attached to the connector, even if the connector cap starts to slide toward the distal end of the connector, the convex portion engages with the two second protruding structures. Therefore, this structure has an advantage in that, because sliding of the convex portion toward the distal end of the connector unintended by a user can be prevented, compared with a structure that does not have the second protruding structures, removal of the connector cap from the connector unintended by a user can be effectively prevented.

Moreover, this structure has an advantage in that, because the two second protruding structures and the first side surface hold the convex portion therebetween, the connector cap can be stably attached to the connector.

A connector according to an eighth aspect of the present disclosure is a connector to which a tubular connector cap, whose distal end is closed, is removably attached. The connector cap includes a connection portion at an end thereof adjacent to an opening thereof, and the connection portion movably connects the connector cap to the connector. A side wall of the connector includes a first groove that extends in an axial direction in which a central axis of the connector extends and that opens outward. The connection portion includes a protruding section that is movably disposed in the first groove and that protrudes toward the central axis. In a state in which the connector cap is attached to the connector, a distal end portion of the connector is inserted from the opening into a space in the connector cap. This structure has advantages similar to those of the first aspect.

A connector cap according to a ninth aspect of the present disclosure is a tubular connector cap that is removably attached to a connector and whose distal end is closed. A side wall of the connector includes a first groove that extends in an axial direction in which a central axis of the connector extends and that opens outward. The connector cap includes a connection portion at an end thereof adjacent to an opening thereof, and the connection portion movably connects the connector cap to the connector. The connection portion includes a protruding section that is movably disposed in the first groove and that protrudes toward the central axis. In a state in which the connector cap is attached to the connector, a distal end portion of the connector is inserted from the opening into a space in the connector cap. This structure has advantages similar to those of the first aspect.

The present disclosure is not limited to the embodiments described above and can be modified in various ways within the scope of the present disclosure described in the claims. The technical scope of the present disclosure includes embodiments that can be obtained by using appropriate combinations of technical elements disclosed in different embodiments. Moreover, new technical features can be formed by using combinations of technical elements disclosed in the embodiments.

The present disclosure contains subject matter related to that disclosed in Japanese Priority Patent Application JP 2018-069143 filed in the Japan Patent Office on Mar. 30, 2018, the entire contents of which are hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. Terminal protection parts comprising:
a connector; and
a tubular connector cap that is removably attached to the connector and whose distal end is closed,
wherein the connector cap includes a connection portion at an end thereof adjacent to an opening thereof, and the connection portion movably connects the connector cap to the connector,
wherein the connection portion is movably connected to the connector in a state in which a concave portion included in one of a side wall of the connector and the connection portion and a convex portion included in the other of the side wall and the connection portion are fitted to each other,
wherein, in a state in which the connector cap is attached to the connector, a distal end portion of the connector is inserted from the opening into a space in the connector cap,
wherein in a bottom part of the concave portion in a depth direction of the concave portion, a second concave portion is formed so as to jut out from a periphery of the bottom part, and
wherein the convex portion includes an engagement section, which engages with the second concave portion, at a distal end thereof.

2. The terminal protection parts according to claim 1, wherein a bottom surface of the concave portion includes a first protruding structure that is outwardly convex, and
wherein, in a state in which the connector cap is attached to the connector, the first protruding structure and a first side surface of the concave portion hold the convex portion therebetween, the first end surface being opposite to a distal end of the connector.

3. The terminal protection parts according to claim 1, wherein a third concave portion is formed at an end of the concave portion, the end being opposite to a distal end of the connector, and the third concave portion extends in a circumferential direction of the connector and communicates with the concave portion, and
wherein the convex portion is disposed so as to be movable also in the third concave portion.

4. The terminal protection parts according to claim 1, wherein the concave portion is included in the side wall of the connector, extends in an axial direction in which a central axis of the connector extends, and opens outward, and
wherein the convex portion is included in the connection portion, protrudes toward the central axis, and is movably disposed in the concave portion.

5. The terminal protection parts according to claim 4, wherein two second side surfaces of the concave portion that extend in the axial direction of the connector each include a second protruding structure that is convex toward a corresponding one of the second side surfaces that the second protruding structure faces, and
wherein, when the convex portion is positioned between the second protruding structures and a first side surface of the concave portion, the first side surface being opposite to a distal end of the connector, the two second protruding structures and the first side surface hold the convex portion therebetween.

6. Terminal protection parts comprising:
a connector; and
a tubular connector cap that is removably attached to the connector and whose distal end is closed,
wherein the connector cap includes a connection portion at an end thereof adjacent to an opening thereof, and the connection portion movably connects the connector cap to the connector,
wherein the connection portion is movably connected to the connector in a state in which a concave portion included in one of a side wall of the connector and the connection portion and a convex portion included in the other of the side wall and the connection portion are fitted to each other,
wherein, in a state in which the connector cap is attached to the connector, a distal end portion of the connector is inserted from the opening into a space in the connector cap, wherein a bottom surface of the concave portion includes a first protruding structure that is outwardly convex, and wherein, in a state in which the connector cap is attached to the connector, the first protruding structure and a first side surface of the concave portion hold the convex portion therebetween, the first end surface being opposite to a distal end of the connector.

7. Terminal protection parts comprising:

a connector; and a tubular connector cap that is removably attached to the connector and whose distal end is closed, wherein the connector cap includes a connection portion at an end thereof adjacent to an opening thereof, and the connection portion movably connects the connector cap to the connector, wherein the connection portion is movably connected to the connector in a state in which a concave portion included in one of a side wall of the connector and the connection portion and a convex portion included in the other of the side wall and the connection portion are fitted to each other, wherein, in a state in which the connector cap is attached to the connector, a distal end portion of the connector is inserted from the opening into a space in the connector cap, wherein a third concave portion is formed at an end of the concave portion, the end being opposite to a distal end of the connector, and the third concave portion extends in a circumferential direction of the connector and communicates with the concave portion, and wherein the convex portion is disposed so as to be movable also in the third concave portion.

8. The terminal protection parts according to claim 7, wherein a protruding structure that is outwardly convex is disposed on a bottom surface of the third concave portion, and wherein, when the convex portion is positioned in the third concave portion, the protruding structure and an end surface of the third concave portion hold the convex portion therebetween, the end surface extending in a direction in which a central axis of the connector extends.

9. Terminal protection parts comprising:

a connector; and a tubular connector cap that is removably attached to the connector and whose distal end is closed, wherein the connector cap includes a connection portion at an end thereof adjacent to an opening thereof, and the connection portion movably connects the connector cap to the connector, wherein the connection portion is movably connected to the connector in a state in which a concave portion included in one of a side wall of the connector and the connection portion and a convex portion included in the other of the side wall and the connection portion are fitted to each other, wherein, in a state in which the connector cap is attached to the connector, a distal end portion of the connector is inserted from the opening into a space in the connector cap, wherein the concave portion is included in the side wall of the connector, extends in an axial direction in which a central axis of the connector extends, and opens outward, wherein the convex portion is included in the connection portion, protrudes toward the central axis, and is movably disposed in the concave portion, wherein two second side surfaces of the concave portion that extend in the axial direction of the connector each include a second protruding structure that is convex toward a corresponding one of the second side surfaces that the second protruding structure faces, and wherein, when the convex portion is positioned between the second protruding structures and a first side surface of the concave portion, the first side surface being opposite to a distal end of the connector, the two second protruding structures and the first side surface hold the convex portion therebetween.

* * * * *